US011826398B2

(12) United States Patent
Daggett et al.

(10) Patent No.: US 11,826,398 B2
(45) Date of Patent: *Nov. 28, 2023

(54) REAGENTS AND METHODS FOR TREATING BACTERIAL INFECTION

(71) Applicant: University of Washington, Seattle, WA (US)

(72) Inventors: Valerie Daggett, Seattle, WA (US); Alissa Bleem, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/326,561

(22) Filed: May 21, 2021

(65) Prior Publication Data

US 2021/0308212 A1 Oct. 7, 2021

Related U.S. Application Data

(63) Continuation of application No. 16/258,505, filed on Jan. 25, 2019, now Pat. No. 11,033,604.

(60) Provisional application No. 62/622,722, filed on Jan. 26, 2018.

(51) Int. Cl.
| | | |
|---|---|---|
| *A61K 38/02* | (2006.01) | |
| *A61K 38/16* | (2006.01) | |
| *A61L 27/34* | (2006.01) | |
| *A61L 29/08* | (2006.01) | |
| *A61L 31/10* | (2006.01) | |
| *C07K 16/00* | (2006.01) | |
| *A61K 9/70* | (2006.01) | |
| *A61P 31/04* | (2006.01) | |
| *A61L 27/22* | (2006.01) | |
| *A61L 27/54* | (2006.01) | |
| *A61L 31/16* | (2006.01) | |
| *A61L 29/16* | (2006.01) | |
| *A61P 41/00* | (2006.01) | |

(52) U.S. Cl.
CPC .............. *A61K 38/16* (2013.01); *A61K 9/70* (2013.01); *A61K 38/02* (2013.01); *A61L 27/22* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61P 31/04* (2018.01); *A61P 41/00* (2018.01); *A61L 2202/24* (2013.01); *A61L 2300/25* (2013.01); *A61L 2300/252* (2013.01); *A61L 2300/404* (2013.01); *A61L 2300/606* (2013.01); *A61L 2420/02* (2013.01); *C07K 16/00* (2013.01)

(58) Field of Classification Search
CPC ......... A61K 38/02; A61K 38/16; A61L 27/34; A61L 27/54; A61L 29/085; A61L 29/16; A61L 2420/00; A61P 31/04; A61P 41/00; C07K 38/02; C07K 38/16
See application file for complete search history.

(56) References Cited

U.S. PATENT DOCUMENTS

| 11,033,604 B2 * | 6/2021 | Daggett .................. A61L 31/10 |
| 2013/0115257 A1 | 5/2013 | Gysemans et al. |
| 2016/0031952 A1 | 2/2016 | Daggett et al. |

FOREIGN PATENT DOCUMENTS

| WO | 2011/031964 A2 | 3/2011 |
| WO | 2012/151554 A1 | 8/2012 |

OTHER PUBLICATIONS

Allegranzi, B. et al. Burden of endemic health-care-associated infection in developing countries: systematic review and meta-analysis. Lancet 377, 228-241 (2011).
Armen, R. S., Alonso, D. O. V. & Daggett, V. Anatomy of an amyloidogenic Intermediate: conversion of β-sheet to α-sheet structure in transthyretin at acidic pH. Structure 12, 1847-1863 (2004).
Armen, R. S., DeMarco, M. L., Alonso, D. O. V. & Daggett, V. Pauling and Corey's α-pleated sheet structure may define the prefibrillar amyloidogenic intermediate in amyloid disease. Proc. Natl Acad. Sci. USA 101, 11622-11627 (2004).
Bagge, N. et al. Pseudomonas aeruginosa biofilms exposed to imipenem exhibit changes in global gene expression and beta-lactamase and alginate production. Antimicrob. Agents Chemother. 48, 1175-1187 (2004).
Bemporad, F. & Chiti, F. Protein misfolded oligomers: experimental approaches, mechanism of formation, and structure-toxicity relationships. Chem. Biol. 19, 315-327 (2012).
Berlon, N. R. et al. Clinical MRSA isolates from skin and soft tissue infections show increased in vitro production of phenol soluble modulins. J. Infect. 71, 447-457 (2015).
Bleem, Alissa et al. "Designed α-sheet peptides suppress amyloid formation in Staphylococcus aureus biofilms" NPJ Biofilms Microbiomes. 2017; 3: 16, (2017).
Blomster-Hautamaa, D. A. & Schlievert, P. M. Preparation of toxic shock syndrome toxin-1. Methods Enzymol. 165, 37-43 (1988).
Boakes, E. et al. Comparative analysis of phenol-soluble modulin production and Galleria mellonella killing by community-associated and healthcare-associated methicillin-resistant Staphylococcus aureus strains. J. Med. Microbio 65, 1429-1433 (2016).
Bryers, J. D. Medical biofilms. Biotechnol. Bioeng. 100, 1-18 (2008).
Centers for Disease Control and Prevention. National and State Healthcare Associated Infections Progress Report (Centers for Disease Control and Prevention, 2016).
Chen, S., Ferrone, F. A. & Wetzel, R. Huntington's disease age-of onset linked to polyglutamine aggregation nucleation. Proc. Natl Acad. Sci. USA 99, 11884-11889 (2002).

(Continued)

*Primary Examiner* — Jeffrey E. Russel
(74) *Attorney, Agent, or Firm* — MCDONNELL BOEHNEN HULBERT & BERGHOFF LLP

(57) ABSTRACT

Disclosed herein are α-sheet peptides and their use for treating a bacterial infection and/or limiting bacterial biofilm formation.

12 Claims, 17 Drawing Sheets

Specification includes a Sequence Listing.

(56) References Cited

OTHER PUBLICATIONS

Childers, M. C., Towse, C.-L. & Daggett, V. The effect of chirality and steric hindrance on intrinsic backbone conformational propensities: tools for protein design. Prot. Eng. Des. Sel 29, 271-280 (2016).
Collins, A.S., 2008. Preventing health care-associated infections.
Daggett, V. Alpha-sheet: the toxic conformer in amyloid diseases? Acc. Chem. Res. 39, 594-602 (2006).
DePas, W. H. & Chapman, M. R. Microbial manipulation of the amyloid fold. Res. Microbiol. 163, 592-606 (2012).
Diego O. Serra, Franziska Mika, Anja M. Richter, Regine Hengge "The green tea polyphenol EGCG inhibits *E. coli* biofilm formation by impairing amyloid curli fibre assembly and downregulating the biofilm regulator CsgD via the σE-dependent sRNA RybB" Molecular Microbiology 2016 vol. 101 Issue 1.
Diego Romero, Edgardo Sanabria-Valentin, Hera Vlamakis, Roberto Kolter "Biofilm Inhibitors that Target Amyloid Proteins" Chemistry and Biology 2013 vol. 20, Issue 1.
Gorman, P. M., Yip, C. M., Fraser, P. E. & Chakrabartty, A. Alternate aggregation pathways of the Alzheimer beta-amyloid peptide: a beta association kinetics at endosomal pH. J. Mol. Biol. 325, 743-757 (2003).
Hopping, G. et al. Designed α-sheet peptides inhibit amyloid formation by targeting toxic oligomers. eLife 3, e01681 (2014).
Horsburgh, M. J. et al. σB modulates virulence determinant expression and stress resistance: characterization of a functional rsbU strain derived from *Staphylococcus aureus* 8325-4. J. Bacteriol. 184, 5457-5467 (2002).
Joo, H.-S., Cheung, G. Y. C. & Otto, M. Antimicrobial activity of community-associated methicillin-resistant *Staphylococcus aureus* is caused by phenol-soluble modulin derivatives. J. Biol. Chem. 286, 8933-8940 (2011).
Kayed, R. et al. Common structure of soluble amyloid oligomers implies common mechanism of pathogenesis. Science 300, 486-489 (2003).
Kellock, J., Hopping, G., Caughey, B. & Daggett, V. Peptides composed of alternating L- and D-Amino acids inhibit amyloidogenesis in three distinct amyloid systems independent of sequence. J. Mol. Biol. 428, 2317-2328 (2016).
Kim, J.Y., Sahu, S., Yau, Y.H., Wang, X., Shochat, S.G., Nielsen, P.H., Dueholm, M.S., Otzen, D.E., Lee, J., Delos Santos, M.M.S. and Yam, J.K.H., 2016. Detection of pathogenic biofilms with bacterial amyloid targeting fluorescent probe, CDy11. Journal of the American Chemical Society, 138(1), pp. 402-407.
Klevens, R. M. et al. Changes in the epidemiology of methicillin-resistant *Staphylococcus aureus* in Intensive care units in US hospitals, 1992-2003. Clin. Infect. Dis. 42, 389-391 (2006).
Klevens, R. M. et al. Estimating health care-associated infections and deaths in U. S. hospitals, 2002. Public Health Rep. 122, 160-166 (2007).
Klevens, R. M. et al. Invasive methicillin-resistant *Staphylococcus aureus* infections in the United States. JAMA 298, 1763-1771 (2007).
Knowles, T. P. J., Vendruscolo, M. & Dobson, C. M. The amyloid state and its association with protein misfolding diseases. Nat. Rev. Mol. Cell. Biol. 15, 384-396 (2014).
Lee, C. C., Walters, R. I. & Murphy, R. M. Reconsidering the mechanism of polyglutamine peptide aggregation. Biochemistry 46, 12810-12820 (2007).

LeVine, H. Thioflavine T interaction with synthetic Alzheimer's disease beta-amyloid peptides: detection of amyloid aggregation in solution. Protein Sci. 2, 404-410 (1993).
Lewis, K. Platforms for antibiotic discovery. Nat. Rev. Drug. Discov. 12, 371-387 (2013).
Ma, H. & Bryers, J. D. Non-invasive determination of conjugative transfer of plasmids bearing antibiotic-resistance genes in biofilm-bound bacteria: effects of substrate loading and antibiotic selection. Appl. Microbiol. Biotechnol. 97, 317-328 (2013).
Mah, T. F. & O'Toole, G. A. Mechanisms of biofilm resistance to antimicrobial agents. Trends Microbiol. 9, 34-39 (2001).
Marinelli, P., Pallares, I., Navarro, S. & Ventura, S. Dissecting the contribution of *Staphylococcus aureus* α-phenol-soluble modulins to biofilm amyloid structure. Sci. Rep 6, 34552 (2016).
Periasamy, S. et al. How *Staphylococcus aureus* biofilms develop their characteristic structure. Proc. Natl Acad. Sci 109, 1281-1286 (2012).
Peschel, A. & Otto, M. Phenol-soluble modulins and staphylococcal infection. Nat. Rev. Microbiol. 11, 667-673 (2013).
Schleeger, M. et al. Amyloids: from molecular structure to mechanical properties. Polymer 54, 2473-2488 (2013).
Schwartz, K., Ganesan, M., Payne, D. E., Solomon, M. J. & Boles, B. R. Extracellular DNA facilitates the formation of functional amyloids in *Staphylococcus aureus* biofilms. Mol. Microbiol. 99, 123-134 (2016).
Schwartz, K., Syed, A. K., Stephenson, R. E., Rickard, A. H. & Boles, B. R. Functional amyloids composed of phenol soluble modulins stabilize *Staphylococcus aureus* biofilms. PLoS Pathog. 8, e1002744 (2012).
Stenvang, M., Dueholm, M.S., Vad, B.S., Seviour, T., Zeng, G., Geifman-Shochat, S., Søndergaard, M.T., Christiansen, G., Meyer, R.L., Kjelleberg, S. and Nielsen, P.H., "Epigallocatechin Gallate Remodels Overexpressed Functional Amyloids in *Pseudomonas aeruginosa* and Increases Biofilm Susceptibility to Antibiotic Treatment" Journal of Biological Chemistry 2016 vol. 291 Issue 51 pp. 26540-26553.
Stewart, P. S. & Costerton, J. W. Antibiotic resistance of bacteria in biofilms. Lancet 358, 135-138 (2001).
Stewart, P. S. Mechanisms of antibiotic resistance in bacterial biofilms. Int. J. Med. Microbiol. 292, 107-113 (2002).
Stowikowski, M. & Fields, G. B. Introduction to peptide synthesis. Curr. Protoc. Prot. Sci. 69:18.1:18.1.1-18.1.13 (2012).
Syed, A. K. & Boles, B. R. Fold modulating function: bacterial toxins to functional amyloids. Front. Microbiol 5, 401 (2014).
Taglialegna, A., Lasa, I. & Valle, J. Amyloid structures as biofilm matrix scaffolds. J. Bacteriol. 198, 2579-2588 (2016).
Tayeb-Fligelman, E. et al. The cytotoxic *Staphylococcus aureus* PSMα3 reveals a cross-α amyloid-like fibril. Science 335, 831-833 (2017).
Towse, C.-L., Hopping, G., Vulovic, I. & Daggett, V. Nature versus design: the conformational propensities of D-amino acids and the importance of side chain chirality. Prot. Eng. Des. Sel 27, 447-455 (2014).
Wang, R. et al. Identification of novel cytolytic peptides as key virulence determinants for community-associated MRSA. Nat. Med. 13, 1510-1514 (2007).
Designed alpha-sheet peptides suppress amyloid formation in *Staphylococcus aureus* biofilms. npj Biofilms and Microbiomes. Published online Jul. 3, 2017. vol. 3, pp. 1-10, plus Supplementary Information. (Year: 2017).

\* cited by examiner

A

B

SEQUENCE LISTING

```
<160> NUMBER OF SEQ ID NOS: 8

<210> SEQ ID NO 1
<211> LENGTH: 23
<212> TYPE: PRT
<213> ORGANISM: Artificial Sequence
<220> FEATURE:
<223> OTHER INFORMATION: Synthetic

<400> SEQUENCE: 1

Arg Gly Glu Met Asn Leu Ser Trp Met Asn Glu Tyr Ser Gly Trp Thr
1               5                   10                  15

Met Asn Leu Lys Met Gly Arg
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic

<400> SEQUENCE: 2

Arg Gly Glu Met Asn Leu Ser Trp Met Asn Glu Tyr Ser Gly Trp Thr
1               5                   10                  15

Met Asn Leu Lys Met Gly Arg
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic

<400> SEQUENCE: 3

Arg Gly Glu Met Asn Leu Cys Trp Met Asn Glu Tyr Ser Gly Trp Cys
1               5                   10                  15

Met Asn Leu Lys Met Gly Arg
            20

<210> SEQ ID NO 4
<211> LENGTH: 23
<212> TYPE: PRT
```

```
<213> ORGANISM: Artificial Sequence
<220> FEATURE:
<223> OTHER INFORMATION: Synthetic

<400> SEQUENCE: 4

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Lys Leu Lys Pro Leu Leu Thr Ser Glu Asn Thr Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Ser Trp Thr Trp Glu Pro Asn Lys Trp Thr Trp Lys
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc
<222> LOCATION: (1)..(1)
<223> OTHER INFORMATION: N-terminal formylation

<400> SEQUENCE: 7

Met Gly Ile Ile Ala Gly Ile Ile Lys Val Ile Lys Ser Leu Ile Glu
1               5                   10                  15

Gln Phe Thr Gly Lys
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic

<400> SEQUENCE: 8

Arg Gly Asn Trp Asn Glu Ser Lys Met Asn Glu Tyr Ser Gly Trp Met
1               5                   10                  15

Leu Met Leu Thr Met Gly Arg
            20
```

REAGENTS AND METHODS FOR TREATING BACTERIAL INFECTION

CROSS REFERENCE

This application is a continuation of U.S. patent application Ser. No. 16/258,505 filed Jan. 25, 2010, now U.S. Pat. No. 11,033,604, issued Jun. 15, 2021, which claims priority to U.S. Provisional Patent Application Ser. No. 62/622,722 filed Jan. 26, 2018, incorporated by reference herein in its entirety.

STATEMENT OF U.S. GOVERNMENT FUNDING

This invention was made with government support under Grant No. GM095808 awarded by the National Institutes of Health. The government has certain rights in the invention

SEQUENCE LISTING STATEMENT

A computer readable form of the Sequence Listing is filed with this application by electronic submission and is incorporated into this application by reference in its entirety. The Sequence Listing is contained in the file created on May 21, 2021 having the file name "19-021-US-CON_Sequence-Listing_ST25.txt" and is 2,641 bytes in size.

BACKGROUND

Nosocomial infections, or healthcare-associated infections (HAIs), are the most common adverse event in healthcare delivery worldwide, leading to significant mortality and financial losses in a variety of settings. In the United States in 2014, approximately one in 25 patients contracted at least one infection during the course of hospitalization, and the frequency of HAIs in developing countries is expected to be at least three times higher than that in the United States.[1,2] This problem is compounded by the fact that approximately 60% of HAIs are associated with biofilm formation.[3] Microbial infections have been observed directly within surgical wounds as well as on nearly all implanted medical devices, including prosthetic heart valves, cardiac pacemakers, cerebrospinal fluid shunts, urinary and intravascular catheters, ocular prostheses, and intrauterine contraceptive devices.[4] When microbes dwell on these surfaces within a biofilm, their susceptibility to antibiotics can decrease by a factor of 10-1000. Sub-lethal doses of antibiotics can actually enhance biofilm formation[5] and the spread of antibiotic resistance genes (typically borne on plasmid DNA), within and between species, is accelerated in biofilm communities, especially when subjected to antibiotic stress.[6,7] Additionally, an increasing number of infectious biofilms are formed by multidrug resistant (MDR) bacteria, and the heterogeneous composition of biofilms likely supports multiple mechanisms of resistance.[8] These issues are further exacerbated by an overall decline in antimicrobial drug development. Indeed, nine classes of antibacterial drugs were introduced between 1936 and 1968, but only five new classes have been approved since then.[9] Therefore, novel approaches are greatly needed to address the problems of biofilm-associated nosocomial infections.

Methicillin-resistant *Staphylococcus aureus* (MRSA), in particular, is major cause of nosocomial infections due to its remarkable versatility and arsenal of virulence factors.[10,11] When *S. aureus* forms a biofilm on a medical device or wound, cells associate with surfaces and each other using a self-produced extracellular matrix (EM) composed of proteins, polysaccharides, and genetic material. There are a variety of proteins in the EM take, but recently phenol soluble modulins (PSMs) have been identified as key factors with dual functionality for *S. aureus* biofilms. In their soluble monomeric form, PSMs have been reported to recruit, activate, and lyse human neutrophils, kill competing bacteria, and promote biofilm dissociation.[12-14]

SUMMARY

In one aspect the disclosure provides methods for treating a bacterial infection, comprising administering to a subject with a bacterial infection an amount effective of an α-sheet peptide to treat the bacterial infection. In one embodiment, the bacterial infection may comprise a bacterial biofilm, and the treating comprises disruption of the biofilm. In another embodiment, the bacterial infection may comprise an *Escherichia coli*, a *Pseudomonas aeruginosa*, or a *Staphylococcus aureus* bacterial infection. In a further embodiment, the bacterial infection may comprise a drug or multi-drug resistant bacterial infection. In another embodiment, the bacterial infection may be contracted during hospitalization. In a further embodiment, the α-sheet peptide comprises one or more peptides including, but not limited to:

SEQ ID NO:1 AP90 RGEmNlSwMNEYSGWtMnL kMGR;
SEQ ID NO:2 AP401 rGeMnLsWmneysGwTmNlKmGr;
SEQ ID NO:3 AP407 RGEmNlCwMNEYSGWcMnL kMGR;
SEQ ID NO:4 AP193 RGEmNyFwMNEYYGWtMnC kMGR; and
SEQ ID NO:8 AP5 RGNwNeSkMNEY-SGWmLmLtMGR.

In another aspect, the disclosure provides methods for limiting development of bacterial biofilm, comprising administering to a subject at risk of a bacterial infection comprising biofilm formation with an amount effective of an α-sheet peptide to limit development of the bacterial biofilm. In one embodiment, the subject may be hospitalized for a surgical procedure. In another embodiment, the surgical procedure may comprise placement of a medical device in the subject. In a further embodiment, the medical device may include, but is not limited to, prosthetic heart valves, cardiac pacemakers, cerebrospinal fluid shunts, urinary catheters, intravascular catheters, ocular prostheses, and intrauterine contraceptive devices. In another embodiment, the α-sheet peptide may be placed on the medical device prior to placement of the medical device in the subject. In a further embodiment, the α-sheet peptide may comprise one or more peptides including, but not limited to:

SEQ ID NO:1 AP90 RGEmNlSwMNEYSGWtMnL kMGR;
SEQ ID NO:2 AP401 rGeMnLsWmneysGwTmNlKmGr;
SEQ ID NO:3 AP407 RGEmNlCwMNEYSGWcMnL kMGR;
SEQ ID NO:4 AP193 RGEmNyFwMNEYYGWtMnC kMGR; and
SEQ ID NO:8 AP5 RGNwNeSkMNEY-SGWmLmLtMGR.

In another aspect, the disclosure provides peptides, comprising the amino acid sequence of a peptide selected from the group consisting of:

SEQ ID NO:2 AP401 rGeMnLsWmneysGwTmNlKmGr;
SEQ ID NO:3 AP407 RGEmNlCwMNEYSGWcMnL kMGR; and SEQ ID NO:4 AP193 RGE<u>m</u>N<u>y</u>F<u>w</u>MNEYYGW<u>t</u>M<u>n</u>C<u>k</u>MGR.

In one embodiment, the peptide comprises the amino acid sequence of RGE<u>m</u>N<u>l</u>C<u>w</u>MNEYSGW<u>c</u>M<u>n</u>L<u>k</u>MGR (SEQ ID NO:3), and the peptide may include a disulfide bond.

In another aspect, the disclosure provides pharmaceutical composition, comprising:
(a) the peptide of any embodiment or combination of embodiments of the disclosure; and
(b) a pharmaceutically acceptable carrier.

In a further aspect, the disclosure provides medical devices comprising one or more α-sheet peptides coated on a surface of the medical device. In one embodiment, the medical devices may include, but are not limited to, prosthetic heart valves, cardiac pacemakers, cerebrospinal fluid shunts, urinary catheters, intravascular catheters, ocular prostheses, and intrauterine contraceptive devices. In another embodiment, the α-sheet peptide may comprise one or more peptide including, but not limited to:

SEQ ID NO:1 AP90 RGE<u>m</u>N<u>l</u>S<u>w</u>MNEYSGW<u>t</u>M<u>n</u>L<u>k</u>MGR;
SEQ ID NO:2 AP401 <u>r</u>GeM<u>n</u>L<u>s</u>W<u>mneys</u>GwT<u>m</u>N<u>l</u>K<u>m</u>G<u>r;</u>
SEQ ID NO:3 AP407 RGE<u>m</u>N<u>l</u>C<u>w</u>MNEYSGW<u>c</u>M<u>n</u>L<u>k</u>MGR;
SEQ ID NO:4 AP193 RGE<u>m</u>N<u>y</u>F<u>w</u>MNEYYGW<u>t</u>M<u>n</u>C<u>k</u>MGR; and
SEQ ID NO:8 AP5 RGNwNeSkMNEYSGWmLmLtMGR.

DETAILED DESCRIPTION

Figure 1:
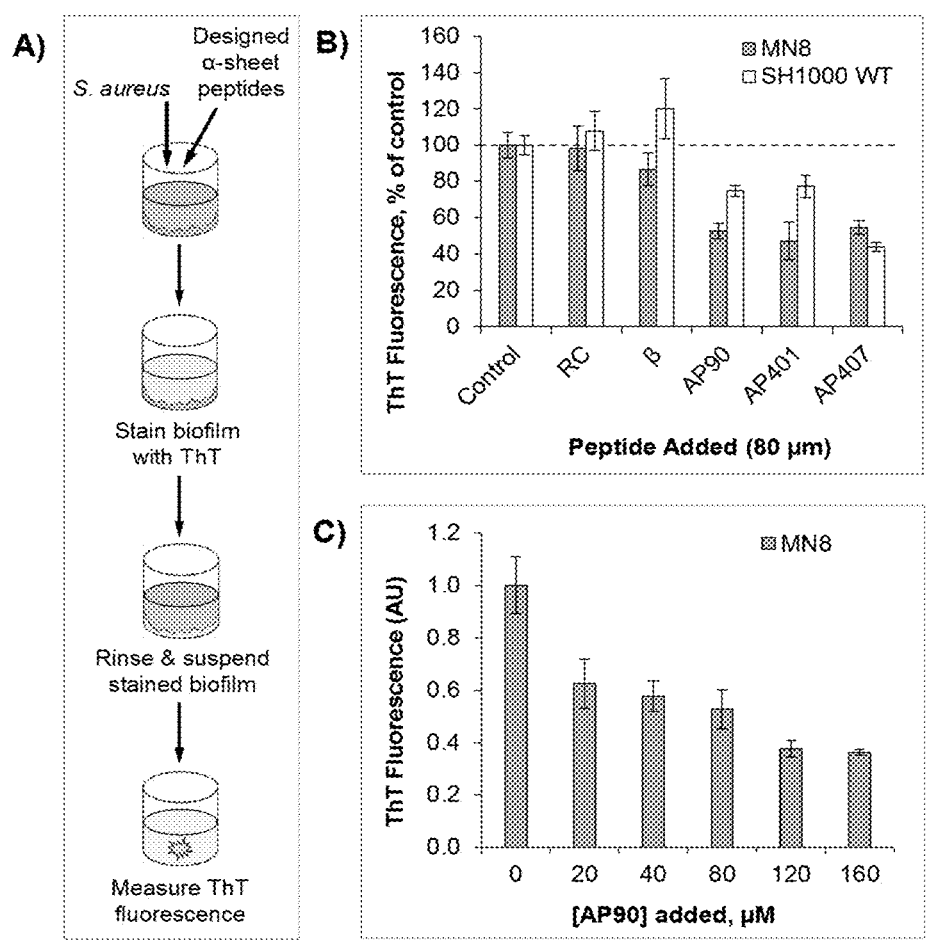
FIG. 1. Screening of designed peptides for prevention of amyloid formation in *S. aureus* biofilms. (A) Schematic of protocol for testing designed α-sheet peptides in *S. aureus* biofilm cultures. (B) A panel of designed α-sheet peptides (AP90, AP401, and AP407), as well as random coil (RC) and β-hairpin controls (β), was tested against two *S. aureus* strains, MN8 (gray bars) and SH1000 WT (white bars). ThT fluorescence values indicate the extent of amyloid formation in the EM and are shown as the percent of peptide-free control conditions. (C) Dose-response curve for the designed peptide AP90 against *S. aureus* MN8 biofilms reveals a significant decrease in EM amyloid content as the concentration of AP90 is increased. Error bars in (B) and (C) represent the standard error of the mean.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). In the various peptides sequences disclosed herein, lower case and underlined letters denote D-amino acids, while upper case letters represent L amino acids, while "G" is achiral.

All embodiments of any aspect of the invention can be used in combination, unless the context clearly dictates otherwise.

In one aspect the disclosure provides methods for treating a bacterial infection, comprising administering to a subject with a bacterial infection an amount effective of an α-sheet peptide to treat the bacterial infection. As demonstrated in the examples that follow, α-sheet peptides are shown to inhibit bacterial biofilm assembly and to disrupt established bacterial biofilm.

The method can be used to treat any suitable bacterial infection, including but not limited to any bacterial infection that may comprise biofilm formation. In one embodiment, the bacterial infection may comprise one or more of an *Escherichia coli*, a *Pseudomonas aeruginosa*, or a Methicillin-resistant *Staphylococcus aureus* (MRSA) bacterial infection. In one embodiment, the *Staphylococcus aureus* bacterial infection may be a methicillin-resistant *Staphylococcus aureus* (MRSA) infection. In a further embodiment, the bacterial infection may comprise a drug or multi-drug resistant bacterial infection. In one embodiment, the bacterial infection may comprise a bacterial biofilm, and the treating may comprise disruption of the biofilm. In other embodiments, the treating may comprise treating the bacteria infection to limit formation of the bacterial biofilm.

As used herein, "treating" means accomplishing one or more of the following: (a) reducing the severity of the infection or extent of the biofilm; (b) limiting or preventing development of symptoms characteristic of the infection or biofilm being treated; (c) inhibiting worsening of symptoms characteristic of the infection or biofilm being treated; (d) limiting or preventing recurrence of the infection or biofilm in patients that have previously had the infection or biofilm; (e) limiting or preventing recurrence of symptoms in patients that were previously symptomatic for the infection or biofilm; and (f) limiting development of the biofilm in a subject at risk of biofilm formation, or not yet showing the clinical effects of the infection or biofilm. Any amount of such "treating" is of great benefit to a subject having a bacterial infection.

In another embodiment, the bacterial infection may be contracted during hospitalization. In the United States in 2014, approximately one in 25 patients contracted at least one infection during the course of hospitalization, and the frequency of healthcare-associated infections (HAIs) in developing countries is expected to be at least three times higher than that in the United States. This problem is compounded by the fact that approximately 60% of HAIs are associated with biofilm formation. Microbial infections have been observed directly within surgical wounds as well as on nearly all implanted medical devices, including prosthetic heart valves, cardiac pacemakers, cerebrospinal fluid shunts, urinary and intravascular catheters, ocular prostheses, and intrauterine contraceptive devices. When microbes dwell on these surfaces within a biofilm, their susceptibility to antibiotics can decrease by a factor of 10-1000. *Staphylococcus aureus*, including but not limited to MRSA, is major cause of nosocomial infections. When *S. aureus* forms a biofilm on a medical device or wound, cells associate with surfaces and each other using a self-produced extracellular matrix (EM) composed of proteins, polysaccharides, and genetic material. Thus, the methods of this aspect of the disclosure are particularly useful for treating subjects that contract a bacterial infection during hospitalization.

Any suitable α-sheet peptide may be used in the methods disclosed herein. In non-limiting embodiments, the α-sheet peptide may comprise one or more peptides including, but not limited to:

SEQ ID NO:1 AP90 RGEmNlSwMNEYSGWtMnLkMGR;
SEQ ID NO:2 AP401 rGeMnLsWmneysGwTmNlKmGr;
SEQ ID NO:3 AP407 RGEmNlCwMNEYSGWcMnLkMGR;
SEQ ID NO:4 AP193 RGEmNyFwMNEYYGWtMnCkMGR; and
SEQ ID NO:8 AP5 RGNwNeSkMNEYSGWmLmLtMGR.

These particular peptides are shown in the examples that follow to be useful for treating bacterial infection and inhibiting formation of and/or disrupting bacterial biofilm formation.

In another aspect, the disclosure provides methods for limiting development of bacterial biofilm, comprising administering to a subject at risk of a bacterial infection comprising biofilm formation with an amount effective of an α-sheet peptide to limit development of the bacterial biofilm. As demonstrated in the examples that follow, α-sheet peptides are shown to inhibit bacterial biofilm assembly. The methods can be used to limit development of biofilm formation in any suitable subject. In one non-limiting embodiment, the subject may be hospitalized, such as for a surgical procedure. In another non-limiting embodiment, the surgical procedure may comprise placement of a medical device in the subject. The methods can be used together with placement of any suitable medical device, including but not limited to prosthetic heart valves, cardiac pacemakers, cerebrospinal fluid shunts, urinary catheters, intravascular catheters, ocular prostheses, and intrauterine contraceptive devices. In another embodiment, the α-sheet peptide may be placed on the medical device prior to placement of the medical device in the subject, or may be administered to the subject prior to, at the time of, and/or after placement of the medical device.

Any suitable α-sheet peptide may be used in the methods of this aspect of the disclosure. In a further embodiment, the α-sheet peptide may comprise one or more peptides including, but not limited to:

SEQ ID NO:1 AP90 RGEmNlSwMNEYSGWtMnLkMGR;
SEQ ID NO:2 AP401 rGeMnLsWmneysGwTmNlKmGr;
SEQ ID NO:3 AP407 RGEmNlCwMNEYSGWcMnLkMGR;
SEQ ID NO:4 AP193 RGEmNyFwMNEYYGWtMnCkMGR; and
SEQ ID NO:8 AP5 RGNwNeSkMNEYSGWmLmLtMGR.

These particular peptides are shown in the examples that follow to be useful for treating bacterial infection and inhibiting formation of and/or disrupting bacterial biofilm formation.

As used herein, "limit" or "limiting development of" means accomplishing one or more of the following in an individual that is at risk one or more of the recited disorders: (a) slowing progression to biofilm formation and/or (b) limiting or preventing development of symptoms characteristic of biofilm formation. Any amount of such "limiting development" is of great benefit to a subject at risk of bacterial biofilm formation.

As used herein, an "amount effective" refers to an amount of the peptide that is effective for treating and/or limiting bacterial infection and/or biofilm formation. The peptides are typically formulated as a pharmaceutical composition, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The peptides can be delivered in a single bolus, or may be administered more than once (e.g., 2, 3, 4, 5, or more times) as determined by attending medical personnel.

In all aspects and embodiments of the methods disclosed herein, the subject may be any suitable subject, including but not limited to mammalian subjects, such as humans.

The peptides may be the sole active agent administered to the subject, or may be administered together (in a single formulation or separately) with one or more other active agents suitable for an intended use.

In another aspect, the disclosure provides peptides, comprising the amino acid sequence of a peptide selected from the group consisting of:

SEQ ID NO:2 AP401 rGeMnLsWmneysGwTmNlKmGr;
SEQ ID NO:3 AP407 RGEmNlCwMNEYSGWcMnLkMGR; and
SEQ ID NO:4 AP193 RGEmNyFwMNEYYGWtMnCkMGR.

These peptides are shown in the examples that follow to be useful for treating bacterial infection and inhibiting formation of and/or disrupting bacterial biofilm formation. In one embodiment, the peptide comprises the amino acid sequence of RGEmNlCwMNEYSGWcMnLkMGR (SEQ ID NO:3), and the peptide may include a disulfide bond.

In another aspect, the disclosure provides pharmaceutical composition, comprising:
(a) the peptide of any embodiment or combination of embodiments of the disclosure; and
(b) a pharmaceutically acceptable carrier.

The pharmaceutical compositions of the invention can be used, for example, in the methods described herein. The pharmaceutical composition may comprise in addition to the peptide(s) (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorhexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions described herein are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

The peptides may be the sole active agent administered in the pharmaceutical composition, or the composition may comprise one or more other active agents suitable for an intended use.

The peptides of the invention can be capped or uncapped, as most appropriate for any given use. In various embodiments, one or both of the N-terminus or the C-terminus of the peptide is acetylated or amidated. In other embodiments, neither the N-terminus nor the C-terminus is capped. The peptides may be linked to other compounds to promote an increased half-life in vivo, such as by PEGylation, HESylation, PASylation, or glycosylation. Such linkage can be covalent or non-covalent.

In a further aspect, the disclosure provides medical devices comprising one or more α-sheet peptides coated on a surface of the medical device. The medical devices can be used, for example, for placement in subjects in need thereof to reduce the risk of bacterial infection/biofilm formation on the medical device. Any suitable medical device can be used, including but not limited to prosthetic heart valves, cardiac pacemakers, cerebrospinal fluid shunts, urinary catheters, intravascular catheters, ocular prostheses, and intrauterine contraceptive devices. Any suitable α-sheet peptide may be used, including but not limited to:

SEQ ID NO:1 AP90 RGEmNlSwMNEYSGWtMnLkMGR;
SEQ ID NO:2 AP401 rGeMnLsWmneysGwTmNlKmGr;
SEQ ID NO:3 AP407 RGEmNlCwMNEYSGWcMnLkMGR;
SEQ ID NO:4 AP193 RGEmNyFwMNEYYGWtMnCkMGR; and
SEQ ID NO:8 AP5 RGNwNeSkMNEYSGWmLmLtMGR.

EXAMPLES

Designed α-Sheet Peptides Inhibit Amyloid Formation in Biofilm Cultures

Figure 7:
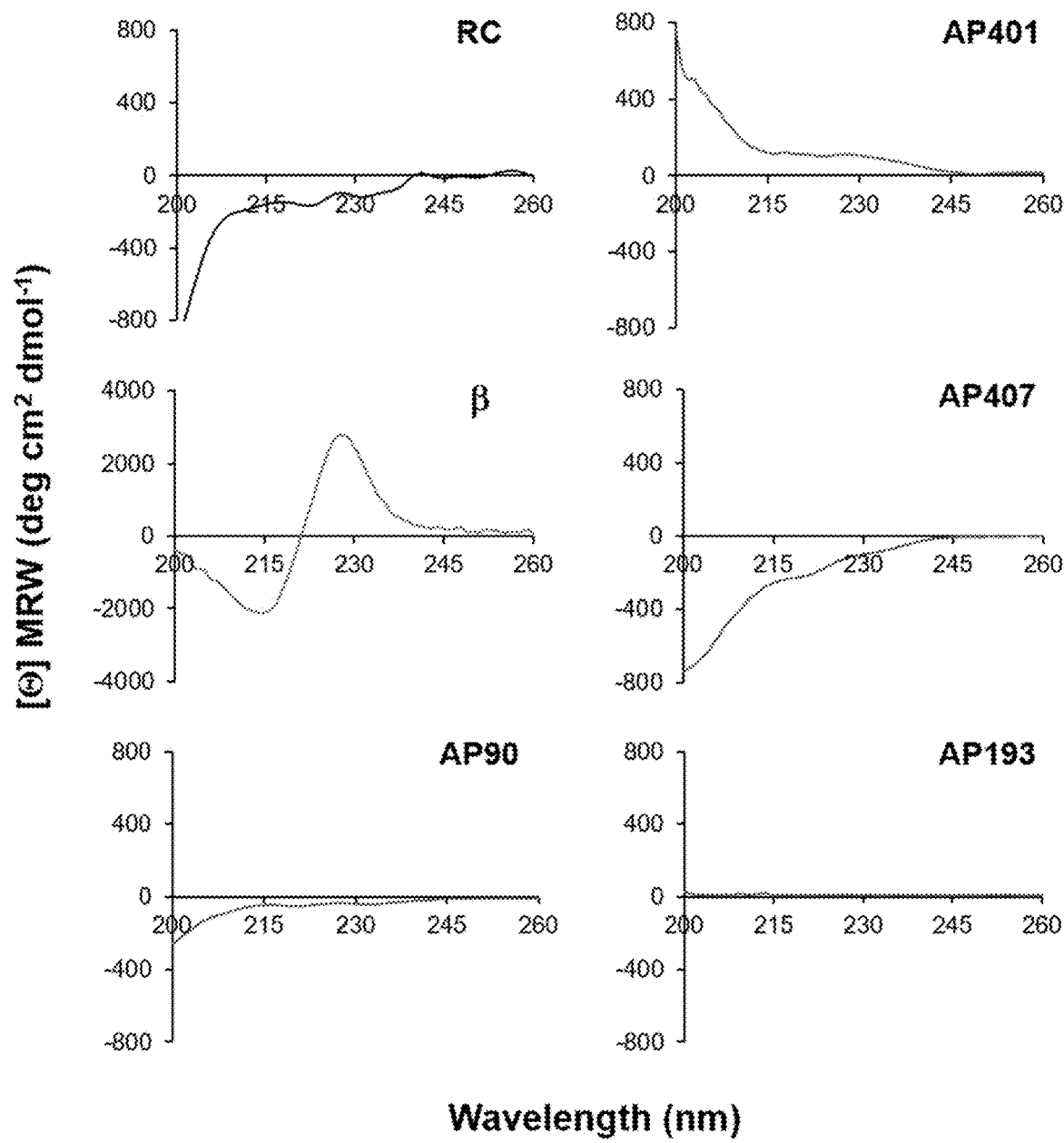
FIG. 7. Graph showing CD spectra of (a) RC, (b) β, (c) AP90, (d) AP401, (e) AP407, and (f) AP193. Peptides were dissolved to a concentration of 10-30 μM in phosphate buffer (or acetate buffer, in the case of β) and spectra were gathered at room temperature.

We developed a novel protocol to identify amyloid fibril formation during biofilm development in two *S. aureus* strains—SH1000 WT, a rsbU+ laboratory strain[27], and MN8, a clinical strain isolated from the human urogenital tract (Table 1). After 24 hours of batch growth in microtiter plates, biofilms were washed and incubated with Thioflavin T (ThT), and the resulting fluorescence signals served as a proxy for the extent of PSM fibril formation in the EM (FIG. 1A). Next, we utilized this assay to test α-sheet amyloid inhibitor designs and control peptides (sequences provided in Table 2) in batch biofilm cultures. The first inhibitor used is AP90 (Alternating Peptide #90, referred to as α1 previously[25,26]). This design does not adopt conventional secondary structure as assessed by circular dichroism (CD), fourier transform infrared spectroscopy (FTIR) and 2D nuclear magnetic resonance (NMR) experiments.[25] Due to the alternating chirality in the strands of the hairpin, there is cancellation of CD the signal, leading to a featureless spectrum, except for negative ellipticity in the so-called random coil region around 195-200 nm due to the L-amino acids in the turn and termini. The AP401 and AP407 designs display similar spectral features by CD, except that AP401 has a positive signal in the random coil region (FIG. 7). AP401 has the same sequence as AP90 but with reversed chirality in the strands and turn, thus the D-amino acids give rise to an approximate mirror image CD spectrum relative to AP90. AP407 is a variant of AP90 with a disulfide bond. An unstructured random coil peptide (RC) and a β-hairpin (β) are used as structural controls.

TABLE 1

Bacterial strains used in this study

| Strain | Description |
|---|---|
| *S. aureus* SH1000 (WT) | Laboratory strain, rsbU+ |
| *S. aureus* MN8 | Clinically relevant strain; urogenital tract |
| *S. aureus* MN8 + mCherry ™ | Transcriptional fusion of RFP to the P3 promoter of strain MN8 |

TABLE 2

Peptide designs used in this study

| Controls | RC (SEQ ID NO:5) | KLKpLLTSENTL |
|---|---|---|
| | B (SEQ ID NO : 6) | SWTWEpNKWTWK |

TABLE 2-continued

Peptide designs used in this study

| | | |
|---|---|---|
| α-sheet Designs | AP90 (SEQ ID:1) | RGEmNlSwMNEYSGWtMnLkMGR |
| | AP401 (SEQ ID NO : 2) | rGeMnLsWmneysGwTmNlKmGr |
| | AP407 (SEQ ID NO : 3) | RGEmNlCwMNEYSGWcMnLkMGR |
| | AP193 (SEQ ID NO : 4 ) | RGEmNyFwMNEYYGWtMnCkMGR |
| | AP5 (SEQ ID NO: 8) | RGNwNeSkMNEYSGWmLmLtMGR |

All designs are single-turn hairpins, with the exception of RC (random coil). The peptides are N- and C-terminally acetylated and amidated, respectively, except for β, which has a free N-terminus. Lower case and underlined letters denote D-amino acids, turn residues are shown in italics, and disulfide-bonded cysteines in AP407 are shown in bold.

Figure 8:
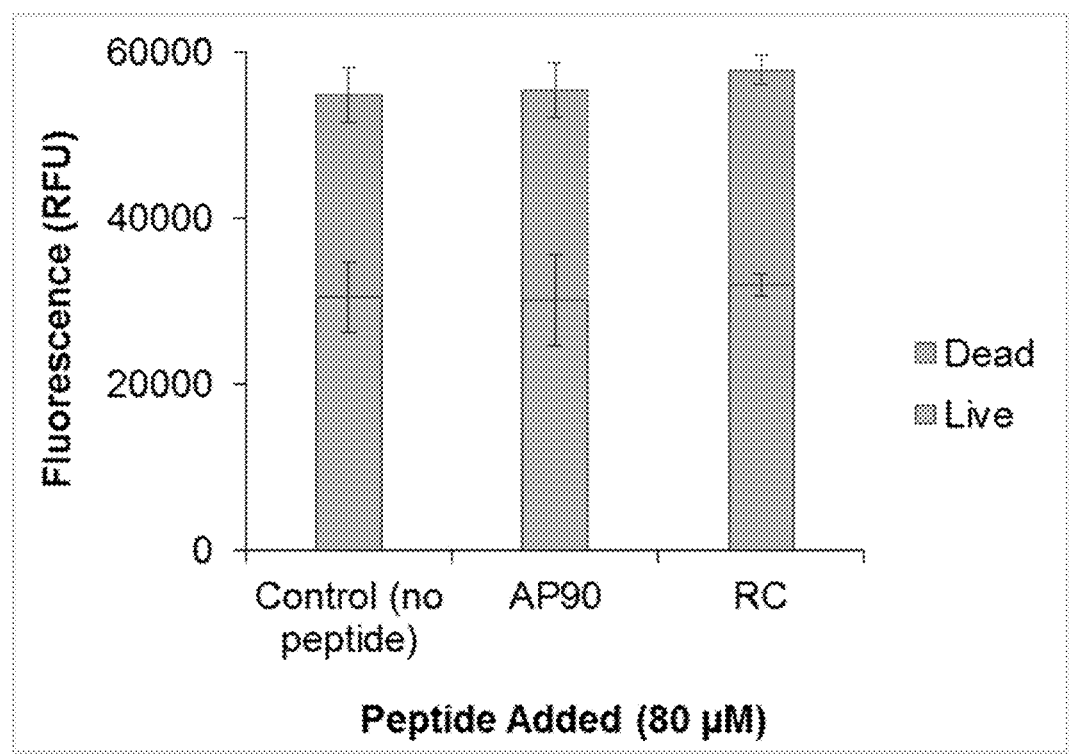
FIG. 8. Graph showing effect of designed peptides applied at a concentration of 80 μM, on the ratio of live:dead cells in liquid cultures of *S. aureus* SH1000 WT.

Designed and control peptides were added to the growth medium prior to inoculation, and biofilms were allowed to grow for 24 hours at 37° C. Planktonic cells were removed and the remaining biofilms were assayed for amyloid content using ThT. The resulting fluorescence signals indicated a significant reduction in amyloid fibril formation in the presence of AP90, AP401, and AP407 (FIG. 1B), particularly for the MN8 clinical isolate. The disulfide-linked peptide design, AP407, reduced the amyloid fibril formation by 46% and 56% in the MN8 and SH1000 WT strains, respectively. In contrast, the random coil and β-sheet control peptides were ineffective. Qualitative assessments of biofilm architecture (e.g. wrinkling) did not appear to change upon addition of peptide inhibitors to the growth medium, and the inhibitors did not alter the ratio of live:dead cells at the concentrations used (FIG. 8). These results suggest that the observed inhibition is due to α-sheet structure rather than an increase in peptide crowding of the extracellular milieu or some other nonspecific effect. Finally, fibril formation decreased in a dose-dependent manner when S. aureus MN8 biofilms were grown with increasing concentrations of AP90 in the culture medium (FIG. 1C).

Figure 2:
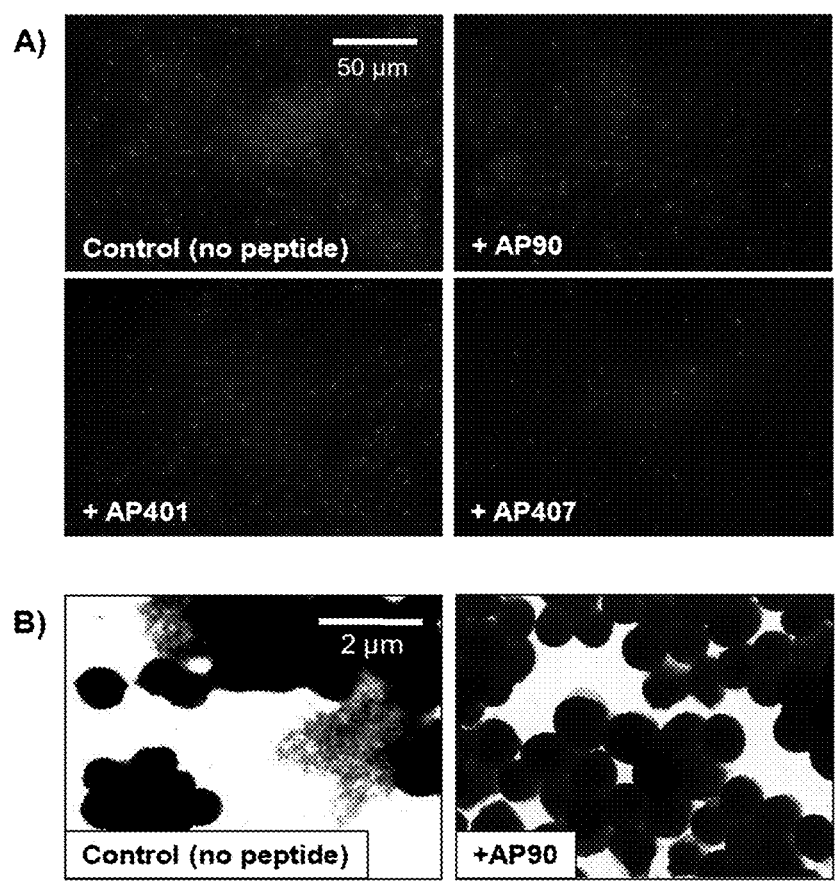
FIG. 2. *S. aureus* biofilm structures become less robust when grown in the presence of designed peptide inhibitors. (A) *S. aureus* MN8+mCherry™ biofilms were grown on glass substrates for 24 hours and then cells were washed and fixed. Addition of peptide inhibitors (80 μM) reduced adhesion to the slide, causing cells to detach during the wash step. Images are representative of duplicate wells. (B) In *S. aureus* SH1000 WT biofilms grown in regular LB medium, PSM amyloid fibrils are visible as deposits in spaces between cells (left). Upon addition of the designed peptide AP90 (80 μM), no extracellular fibril deposits were observed (right).

Designed Peptide Inhibitors Disrupt the Structural Integrity of S. aureus Biofilms To further investigate the ability of designed peptides to inhibit PSM amyloid formation, fluorescent (mCherry™) MN8 biofilms were grown in culture plates with glass bottom wells. After 24 hours at 37° C. the biofilms were gently rinsed with pipetted saline to remove unattached biomass and the remaining attached cells were fixed and imaged. A robust biofilm formed on the glass at the bottom of each well in LB medium alone (FIG. 2A); in contrast, there was significant disruption of the biofilm in the presence of the α-sheet compounds. AP407, for example, caused nearly all of the biofilm to detach from the slide upon rinsing. These qualitative results are in good agreement with the quantitative results obtained for amyloid inhibition in FIG. 1B. Addition of anti-α-sheet peptides triggered a significant reduction in PSM amyloid formation as measured by ThT fluorescence and also served to weaken the S. aureus biofilms by reducing the PSM amyloid fibril content of the extracellular matrix. To further confirm the observed reduction in matrix stability upon treatment with α-sheet peptides, S. aureus SH1000 WT biofilms were examined with transmission electron microscopy (TEM). Deposits of PSM fibrils were clearly visible in the spaces around S. aureus cells; however, in the presence of AP90, amyloid fibrils could not be found (FIG. 2B).

Amyloid Formation by PSMα1 is Characterized by Structural Changes

Figure 3:
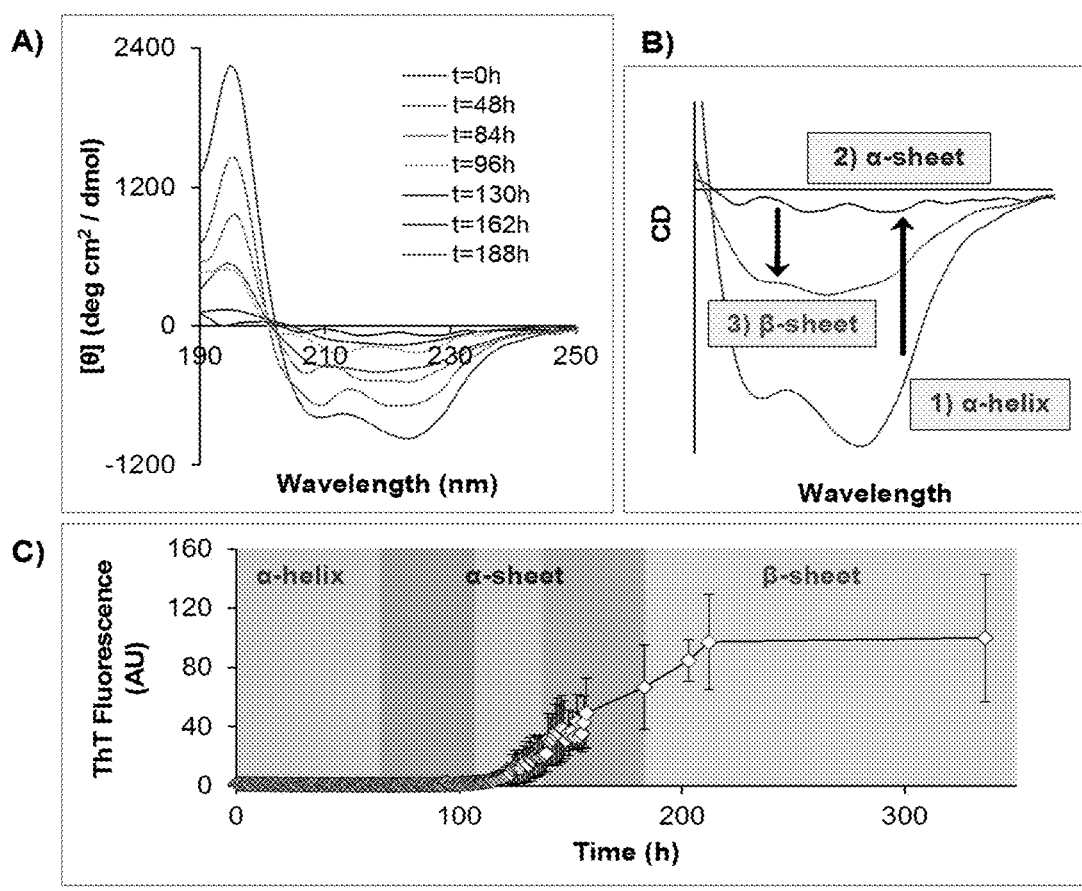
FIG. 3. CD measurements capture structural transitions of PSMα1. (A) CD spectra of PSMα1 samples (30 μM, solubilized in 0.13% HFIP, potassium phosphate buffer, pH 5, without ThT) were taken periodically during aggregation. At early time points (t=0, 48, 84 h), negative peaks at ~208 and 220 nm represent α-helical secondary structure. At intermediate time points (t=130 h), featureless spectra indicate formation of α-sheet, and by the end of the time course (t=188 h) a negative peak at ~218 nm signals the presence of β-structure. (B) Close-up view of characteristic CD spectra for α-helix (0 h), α-sheet (130 h), and β-sheet (188 h). (C) Aggregation of synthetic PSMα1 peptides (30 μM, same conditions as for CD but contains ThT) was tracked over time by ThT fluorescence in a microtiter plate. Error bars in (C) represent the standard deviation of the mean of four samples.
Figure 4:
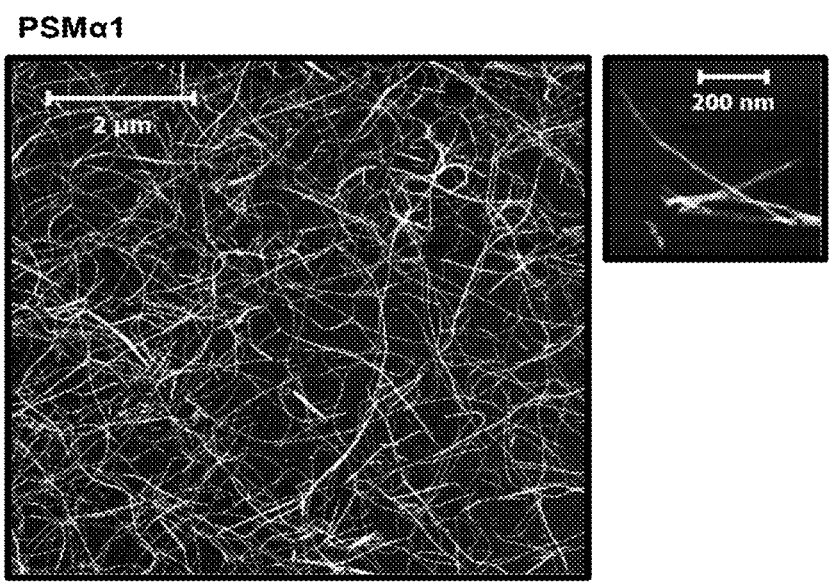
FIG. 4. AFM image of synthetic PSMα1 amyloid fibrils. PSMα1 peptide samples were allowed to aggregate at high concentrations (~400 μM), and the resulting fibrils exhibited extensive surface coverage, with each fibril measuring approximately 10 nm in diameter and 0.1-4 μM in length.

To further characterize the binding of designed α-sheet peptides to PSMs, we quantified the structural transition of a synthetic PSM peptide as it aggregated to form amyloid fibrils in solution. Dilute solutions of PSMα1 (30 μM) were incubated at 37° C. and CD spectra were collected to determine the conformational species populated during aggregation (FIG. 3A,B). Simultaneously, aggregation was monitored in matched PSMα1 samples in a microtiter plate (FIG. 3C). At the beginning of the time course, PSMα1 peptide displayed a characteristic α-helical spectrum by CD, with minima at approximately 208 and 222 nm. With time, however, the α-helical content decreased, as evidenced by the progressive decrease in the helical signal as it became less negative through the first 100 hours. As mentioned above, α-sheet gives rise to a featureless CD spectrum and the PSMα1 spectrum at 130 h is very similar to those of the designed α-sheet peptides (FIG. 7). Prior to this time, there appeared to be progressive conversion of α-helix to α-sheet such that the mixing led to lifting of the helical signal until full conversion occurred. Notably, the "flattened" α-sheet spectrum coincided with the onset of fibril formation. As aggregation proceeded, a β-sheet CD signal appeared at ~217 nm. The onset of fibril formation (the length of the lag period) was inversely proportional to the concentration of the sample (data not shown). As further confirmation of the presence of amyloid fibrils, PSMα1 was allowed to aggregate at a higher concentration (440 μM) and the resulting samples were examined with Atomic Force Microscopy (AFM). Mica substrates exhibited extensive surface coverage by a dense network of amyloid fibrils, each measuring approximately 10 nm in diameter and 0.1-4.0 μm in length (FIG. 4).

Designed α-Sheet Peptides Inhibit Amyloid Formation Through Selective Binding

Figure 5:
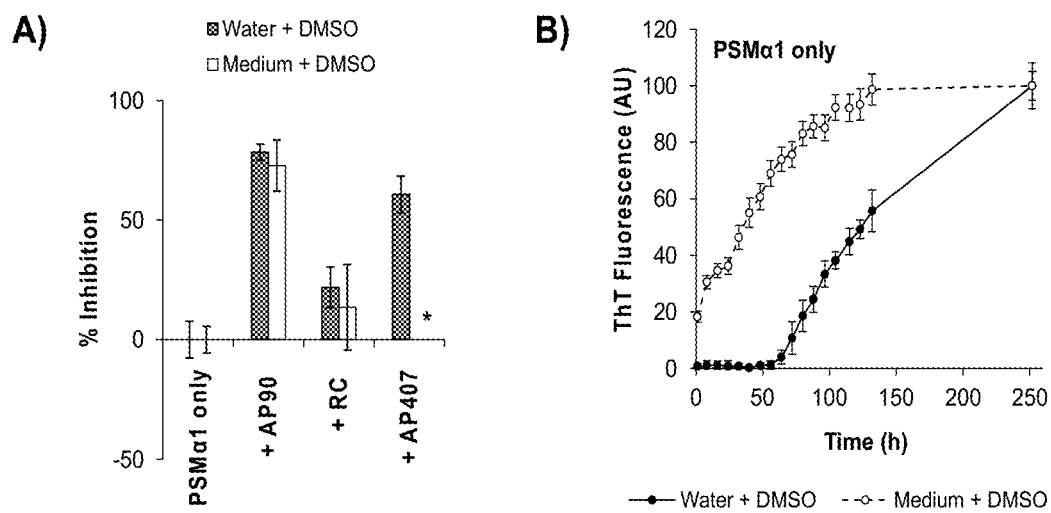
FIG. 5. Aggregation of synthetic PSMα1 is inhibited by designed α-sheet peptides. (A) Synthetic PSMα1 peptide (30 μM, <1% DMSO, pH 5.5) was allowed to aggregate alone and in the presence of AP90 (1:4 molar ratio), RC (1:4 molar ratio), or AP407 (1:3 molar ratio). Two different solvent conditions were used (water+<1% DMSO, gray bars; LB medium+<1% DMSO, white bars) and aggregation was monitored by ThT fluorescence. Inhibition values for each peptide are reported as a percentage of the peptide-free control samples (0% inhibition). (B) ThT fluorescence curves monitored the aggregation kinetics of PSMα1 under two different solvent conditions (water+<1% DMSO, black circles; LB medium+<1% DMSO, white circles). Fluorescence values in (B) are averages of 3-6 samples, with error bars to represent the standard deviation of the mean. Error bars in (A) represent the standard error of the mean. * indicates that AP407 was not tested in the LB medium+<1% DMSO solvent conditions.

After establishing the structural transitions required to form amyloid in PSMα1, we examined the effect of the designed α-sheet peptides on the aggregation of PSMα1 in vitro. The designed peptide inhibitors were co-incubated with freshly prepared samples of synthetic PSMα1 (30 μM) and aggregation was monitored by ThT, as described above. To ensure sample homogeneity and removal of any amyloid "seeds" prior to aggregation, the synthetic PSMα1 peptide was treated with DMSO and then diluted into filtered water. As shown in FIG. 5A (gray bars) addition of excess AP90 at a 1:4 molar ratio inhibited PSMα1 amyloid formation by 81±5%. Similarly, AP407 showed 69±9% inhibition when added at a 1:3 ratio. The random coil peptide control (RC), meanwhile, had little effect on PSMα1 aggregation.

Given the differences between the conditions of these in vitro aggregation reactions in filtered water and those in the S. aureus biofilm cultures, we investigated the effect of LB medium on the behavior of PSMα1 with and without peptide inhibitors. As shown in FIG. 5B, LB medium greatly increased the kinetics of fibril formation, effectively abolishing the lag. In contrast, solubilization of PSMα1 in HFIP, which is known to stabilize α-helical structure, dramatically increased the lag time (compare FIGS. 3C and 5B). Nevertheless, AP90 inhibited fibril formation in LB medium (73±11 when applied at a 1:4 molar ratio). Once again, addition of the random coil peptide control (RC) had did not significantly influence amyloid formation under these conditions.

Figure 6:
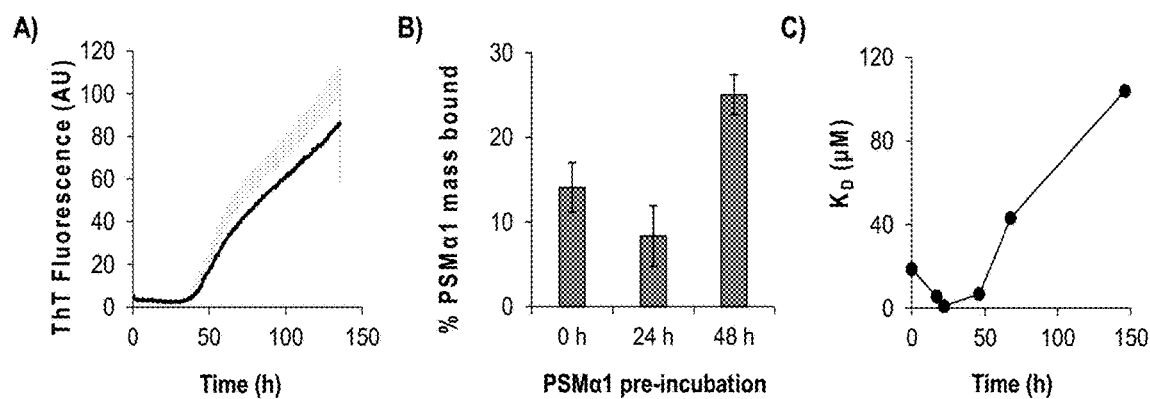
FIG. 6. Designed α-sheet peptides preferentially bind α-sheet-rich PSMα1 over fresh or fibrillar PSMα1. (A) Synthetic PSMα1 peptides (30 μM) were allowed to aggregate as in FIG. 5, and ThT-free samples were removed periodically from the plate for binding assessment using an agarose bead, resin-based assay and biolayer interferometry. Error bars represent the standard deviation of six samples. (B) In the resin-based assay, AP193-functionalized beads preferentially bound α-sheet rich PSMα1 (48 h) over earlier time points (0 and 24 h). Error bars represent the standard error of the mean. (C) In BLI experiments, the equilibrium dissociation constant, $K_D$, indicates preferential binding between AP90 and α-sheet-rich PSMα1 (~48 h) as opposed to α-helix-rich (~0 h) or β-sheet-rich states (~150 h). Note that 150 h is still in the sigmoidal region of the transition and some α-sheet is present.

To further probe the interactions between PSMα1 and designed α-sheet peptides, we immobilized a hydrophobic AP90 derivative—termed AP193—on agarose beads and applied solutions of either fresh (completely solubilized) or pre-incubated PSMα1 (allowed to aggregate for 24 or 48 h). The use of a slightly more hydrophobic peptide design enabled better coupling efficiency between the lysine and aldehyde functional groups on the bead surfaces (94% coupling efficiency with AP193 versus 63% efficiency with AP90) while maintaining the desired α-sheet design structure. After functionalization with AP193, any remaining aldehyde sites on the beads were blocked with Tris buffer, and fresh or pre-incubated PSMα1 samples were allowed to interact with the beads for 2 hours at room temperature. The bead mixtures were contained within a micro-spin column, so the system was treated as a packed bed reactor and a series of phosphate buffered saline (PBS) washes was used to remove unbound PSMα1 from the column. The total protein content of each wash volume was measured with a fluorescence-based assay, and these values were summed to generate a mass balance for PSMα1 on the packed bed. All measurements were normalized by a control experiment in the absence of immobilized peptide. Pre-incubated PSMα1 samples were prepared identically to those in FIG. 6A, and they were applied to the columns after 24 or 48 hours of incubation. According to CD (FIG. 3), we expect PSM α-sheet structures to become enriched near the end of the aggregation "lag phase", which occurs between 45 and 50 hours in FIG. 6A. As shown in FIG. 6B, pre-incubated PSMα1 was preferentially bound over fresh and helical PSMα1. Thus, increased binding and retention of pre-incubated (48 h) PSMα1 samples is consistent with increased α-sheet content in these samples. This conclusion was explored further using biolayer interferometry (BLI). BLI is an optical technique that analyzes interference patterns based on adsorption of protein samples to a biosensor tip. For this study, AP90 (180 µM) was immobilized on the aminopropylsilane (APS) tip, and then the association and dissociation of PSMα1 (50 µM) was measured at various time points during aggregation. In good agreement with the agarose bead-binding experiments, PSMα1 samples near the end of the aggregation lag phase displayed the highest binding affinity with equilibrium dissociation constants of 1-1.5 µM (FIG. 6B,C). Conversely, the binding affinity dropped by two orders of magnitude as PSMα1 converted to β-sheet (146 h), but note that this is in the transition region between α-sheet and β-sheet and we were unable to determine accurate values for aggregated material.

Discussion

PSMs can aggregate to form functional amyloid fibrils that stabilize biofilms and provide resistance to disruption[15], which is critical to the virulence of medical device-associated infections. The prevalence of PSMs in drug-resistant infections[28], combined with their ability to influence biofilm development, makes them an attractive target for therapeutic intervention. However, there have been no efforts to date to inhibit PSM amyloid formation.

In this study, we have demonstrated a novel approach to suppress amyloidogenesis in the *S. aureus* biofilm matrix through the use of de novo α-sheet peptides. The designed α-sheet peptides inhibited amyloid formation in both a laboratory strain of *S. aureus* (SH1000 WT) as well as a human urogenital clinical isolate (MN8), and the effect was dose-dependent. In fact, all of the α-sheet designs inhibited fibril formation, while the random coil and β-hairpin control peptides did not. Furthermore, inhibition was accompanied by a weakening of the biofilm matrix. Interestingly, while ThT fluorescence indicated that our AP90 design inhibited amyloid formation by 47% in *S. aureus* MN8 biofilms, no amyloid fibrils were visible when these biofilms were examined by TEM. This suggests that ThT may bind to other species in addition to the amyloid fibrils or that smaller ThT-binding protofibrils may be present but not visible in the TEM images.

In vitro, fully aggregated PSMα1 forms abundant fibrils approximately 10 nm in diameter and 0.1-4.0 µm in length. These dimensions correlate with those of mammalian amyloid fibrils, which typically span 10 nm in width (with a range of 5-25 nm) and up to 10 µm in length[30]. To our knowledge, these are the first AFM images of PSM fibrils, confirming that their size and morphology are indeed amyloid-like.

Herein, we have also taken the first steps to elucidate the biophysics underlying the conversion of soluble, monomeric PSMs to insoluble, polymeric fibrils. We have shown with CD that the PSMα1 peptide undergoes conformational changes as it aggregates, progressing from α-helix→α-sheet→β-sheet fibrils. Correspondingly, our designed anti-α-sheet peptides, which are themselves α-sheet, target the intermediate α-sheet structure of PSMα1 and inhibit amyloid fibril formation in vitro. The conformational equilibria are complicated, but we observed entry and exit from α-sheet occurring just prior to the onset of a steep increase in ThT binding, with mixed populations before and after with α-helix and β-sheet, respectively. The end of the lag phase of aggregation was also associated with preferential binding of α-sheet-rich PSMα1 samples to beads functionalized with AP193, as well as the increased binding affinity observed by BLI. In the latter case, the binding of α-sheet-enriched PSMα1 to AP90 is two orders of magnitude stronger than the binding observed with substantial amounts of β-sheet present and polymerized PSMα1. While not being bound by any mechanism of action, the CD, column-binding, and BLI experiments reinforce our hypotheses that amyloid formation by PSMα1 is characterized by formation of α-sheet structures and that the interaction between designed α-sheet peptides and PSMα1 is structure-specific.

Aggregation studies of synthetic PSMα1 in two different solvent conditions—aqueous and growth medium—demonstrate that the α-sheet structure of AP90 and AP407 is critically important for inhibition, while no appreciable inhibition is observed for random coil controls. The polymerization lag phase is eliminated when synthetic PSMα1 is allowed to aggregate in LB growth medium, suggesting that components of the growth medium accelerated aggregation, but inhibition by AP90 persisted. These observations demonstrate that specific interactions between PSMs and the designed α-sheet inhibitors disclosed herein lead to a reduction of amyloid fibril content in *S. aureus* biofilm cultures. Thus, the peptides and methods disclosed herein reduce the amyloid content of the biofilm matrix, rendering the biofilms less robust. Additionally, by removing the structural reinforcement of the biofilm EM provided by amyloid fibrils, these peptides and methods can mitigate problems with antibiotic transport and associated resistance.

CONCLUSIONS

We show that the assembly of bacterial biofilm is inhibited by designed α-sheet peptides and that the main proteinaceous component of the *S. aureus* amyloid fibrils, PSMα1, adopts α-sheet, supporting our inhibitor design premise to provide a complementary α-sheet surface for the use of α-sheet peptides as inhibitors. Thus, the methods disclosed herein are applicable to a variety of different functional bacterial amyloid systems including *Escherichia coli* and *Pseudomonas aeruginosa*, and can be used as therapeutic agents for biofilm-associated infections.

Figure 10:
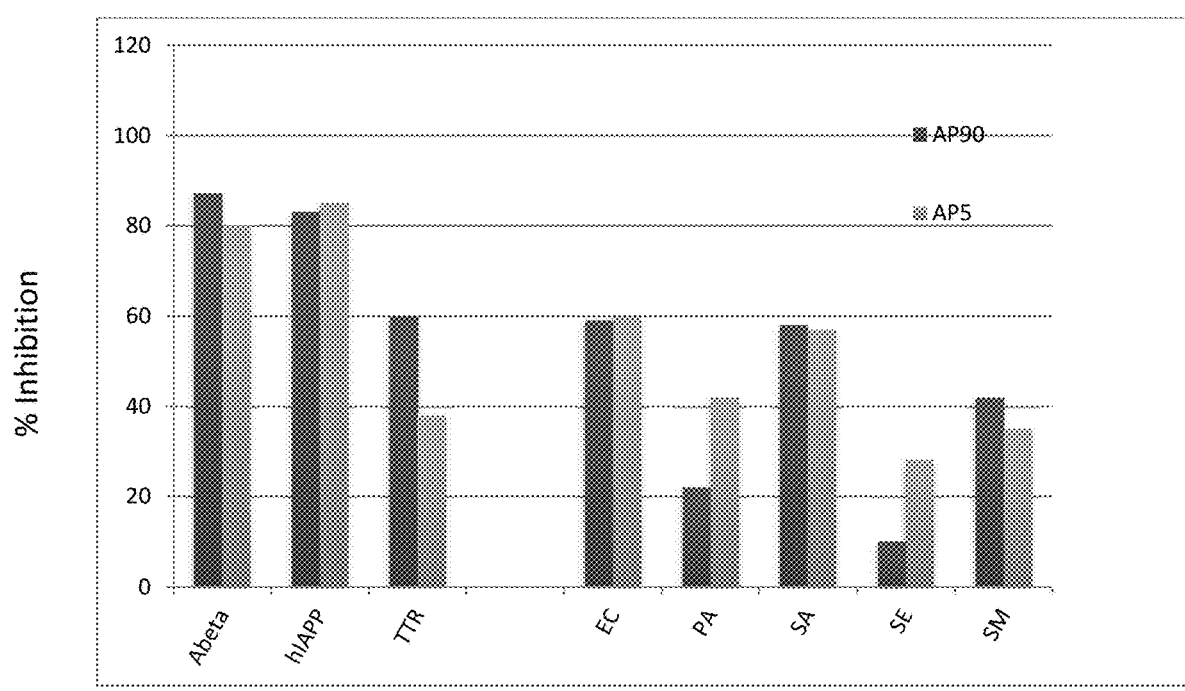
FIG. 10. Graph showing effect of designed peptides on amyloid formation in known human disease-associated proteins and in live bacterial cells.

The exemplary α-sheet inhibitors were also tested against other exemplary biofilm-forming bacteria, namely *Pseudomonas aeruginosa* (PA), *Escherichia coli* (EC), *Staphylococcus epidermidis* (SE), and *Streptococcus mutans* (SM), and they show inhibition using a conventional crystal violet biofilm assay (FIG. 10), which shows inhibition with AP90 (SEQ ID NO:1) and AP5 (SEQ ID NO:8) against both SA and PA, bacterial species that express two totally different amyloid precursor proteins, and with one being gram-negative and one gram-positive. Furthermore, these same inhibitors are active against EC, SE, and SM.

*Escherichia coli* (curli)

*E. coli* assemble adhesive amyloid fibers called curli that stabilize the biofilm extracellular matrix (EM) and facilitate adhesion to inert surfaces as well as neighboring cells. Assembly of curli is coordinated by two operons encoding a total of seven genes, but the major amyloid subunit is a 13 kDa protein called CsgA.

For inhibition assays with CsgA, purified, recombinant CsgA was desalted from a stock solution containing 8 M Gnd HCl into 50 mM potassium phosphate buffer (KPi, pH 6.2) and diluted to a final concentration of 0.2 mg/m L. Samples were aliquoted into 96 well plates and incubated quiescently at 25° C. Plates were removed for periodic measurements in a plate reader, where the fluorescence of Thioflavin T (ThT) was used to monitor protein fibril formation in real time. ThT fluoresces upon binding β-sheet structure and serves as a proxy for amyloid fibril content. Samples without ThT were also incubated in the same plate, and these were removed periodically for circular dichroism (CD) spectra measurements. α-sheet secondary structure displays a unique spectral signature by CD, where alternation of subsequent residues between αL and αR backbone conformation leads to a nearly flat spectrum, produced by cancellation of the alternately polarized light.

Figure 11:
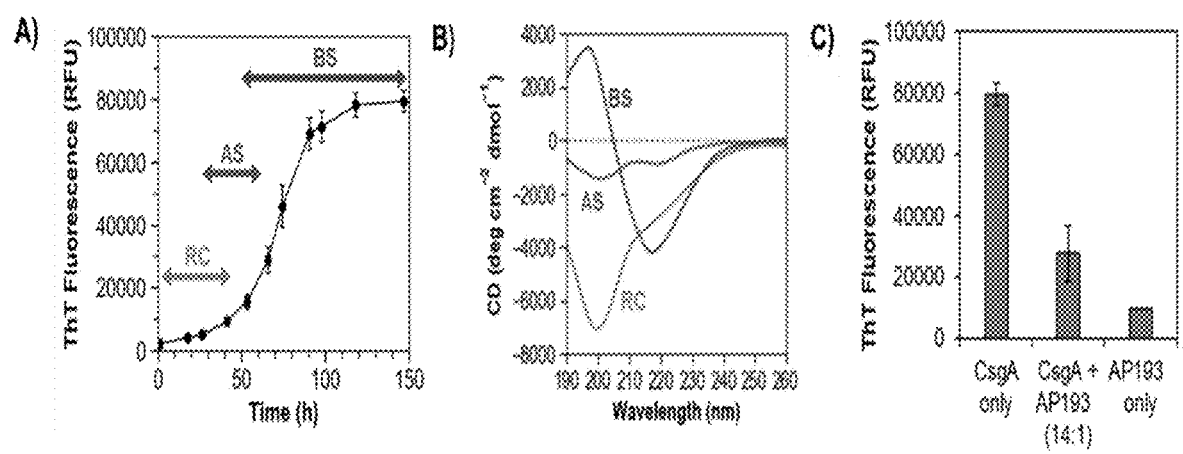
FIG. 11. A) CsgA aggregation monitored by ThT fluorescence. (B) Structural transitions observed by CD are indicated as follows: RC=random coil (spectrum collected after 1 h incubation), AS=α-sheet (spectrum collected after 32 h incubation), BS=β-sheet (spectrum collected after 150 h incubation). (C) Endpoint (150 h) fluorescence values for samples of CsgA alone, CsgA and AP193 (14:1 molar ratio), and AP193 alone indicate that addition of synthetic α-sheet peptide inhibits CsgA aggregation. Error bars represent one standard deviation from the mean of three replicates.

CsgA aggregates with sigmoidal kinetics (FIG. 11A). Under these experimental conditions, a lag period of approximately 40 h was followed by a rapid increase in ThT fluorescence, corresponding to the accumulation of amyloid fibrils. Fibril formation continued until reaching a plateau in ThT fluorescence, typically around 150 h of incubation. These three phases of the aggregation process corresponded to unique secondary structure characteristics in the CsgA protein, as measured by CD. At the beginning of the assay, CsgA was highly soluble, with low ThT fluorescence values and mostly random-coil secondary structure (FIG. 11A,B). Near the inflection point between the lag and the exponential increase in ThT fluorescence, CsgA samples contained oligomers enriched in α-sheet secondary structure (FIG. 11A, B, shading/lines). Finally, at the end of the assay when ThT fluorescence had reached a plateau, CsgA exhibited clear β-sheet structure by CD and insoluble amyloid fibrils were visible to the naked eye (FIG. 11A,B). In some samples, the dimeric α-sheet peptide AP193 was also added to the mixture at a molar ratio of 14:1 (CsgA:AP193). After 150 h incubation, the extent of amyloid formation in the two samples was measured by ThT fluorescence (FIG. 11C). As expected, CsgA alone demonstrated a high degree of fibril formation and large ThT fluorescence values. When incubated with AP193, however, CsgA fibril formation was significantly reduced. This inhibition was attributed to an interaction between the two components: the synthetic α-sheet peptide recognizes α-sheet-rich oligomers that arise during CsgA aggregation, sequestering these soluble species and abrogating their further association into fibrils.

Binding Assays

Synthetic α-sheet peptides inhibit aggregation of amyloidogenic proteins and peptides by binding soluble oligomers formed by these targets as they polymerize. To establish the emergence of α-sheet content during aggregation, we developed a soluble oligomer-binding assay (SOBA), an ELISA-like assay that utilizes a synthetic α-sheet peptide (AP193) instead of an antibody as the capture agent. SOBA sensitively detects α-sheet content in oligomeric samples, but not in corresponding monomeric or fibrillar samples. Thus, SOBA represents an indirect method to detect α-sheet structure due to binding complementarity between α-sheet structure in the synthetic peptide and α-sheet structure in the oligomeric target. In a more quantitative approach, binding constants (e.g. equilibrium binding constant, $K_D$) between synthetic α-sheet peptides and amyloid targets can be measured with biolayer interferometry (BLI). This optical technique is similar to surface plasmon resonance (SPR), and it uses white light to detect changes in interference upon binding. Both binding assays—SOBA and BLI—can be applied to samples of CsgA as it aggregates.

In Situ Inhibition Assays

Biofilms of the cystitis *E. coli* isolate UTI89 were cultivated in YESCA broth with 4% DMSO at 26° C., conditions which are known to elicit increased curli biogenesis. Varying doses of the dimeric α-sheet peptide, AP193, were also added to the cultures at the time of inoculation. AP193 is covalently linked through a single cysteine in each of its constituent monomers. Since DMSO was already present in the biofilm growth medium, AP193 stocks were supplemented with 4% DMSO to improve solubility, and the buffer solution was maintained at high pH (sodium carbonate, pH 9.6) to retain oxidation of the disulfide bond. After 48 hours of growth, biofilms were washed, homogenized, and stained with ThT.

Figure 12:
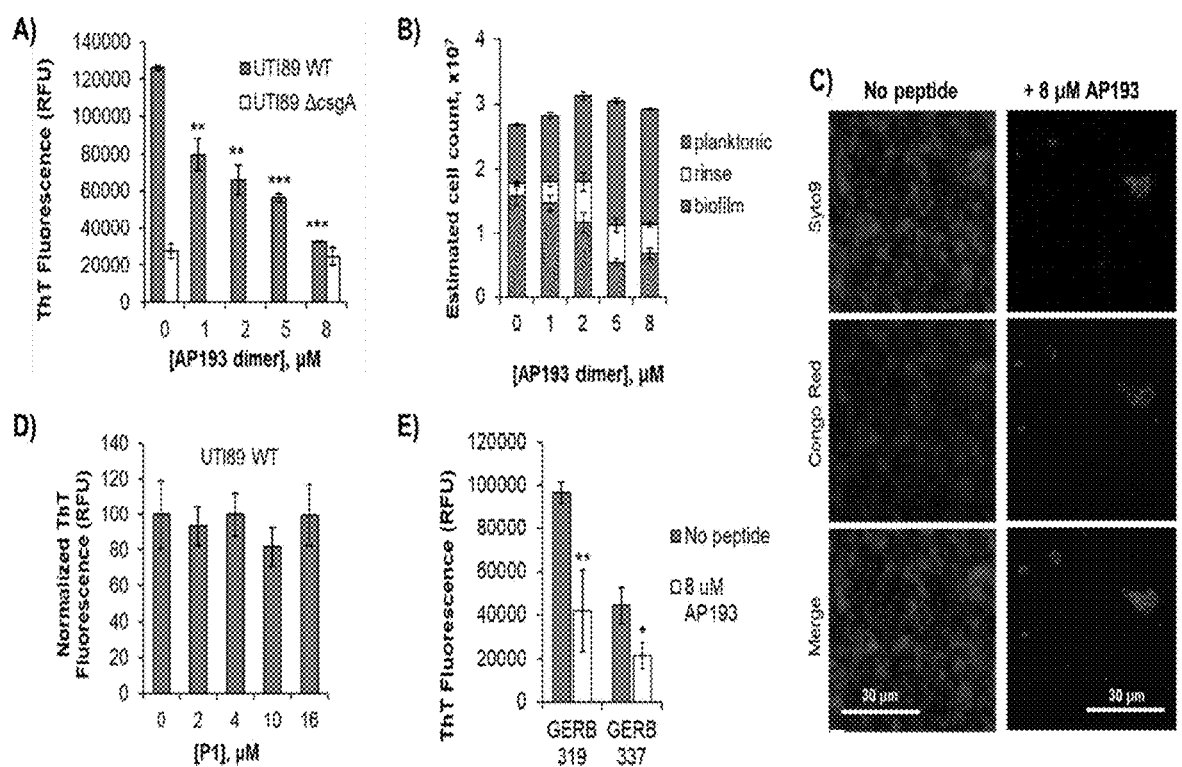
FIG. 12. Synthetic α-sheet peptides inhibit amyloid formation in uropathogenic *E. coli* biofilms. A) ThT assay demonstrates a dose-dependent decrease in EM amyloid content when biofilms are cultivated in the presence of AP193 (gray bars=UTI89 WT; white bars=UTI89 ΔcsgA). B) Addition of AP193 does not kill bacteria or inhibit their growth; rather, the proportion of cells residing in the biofilm state is reduced. C) UTI89 WT biofilms are far less adherent to glass slides when grown in the presence of AP193. D) The unstructured synthetic peptide, P1, does not demonstrate any appreciable inhibition of amyloid formation in UTI89 WT. E) AP193 is also effective in reducing the EM amyloid content of two clinical isolate strains, GERB 319 and GERB 337. Error bars indicate standard deviation of the mean of at least three replicates. Significance values are $p<0.05$: *, $p<0.01$: , $p<0.001$: *.

In biofilms comprised of a UTI89 ΔcsgA knockout strain that lacks the ability to produce curli, no significant changes were observed upon addition of AP193 (FIG. 12A, white bars). Conversely, in curliated UTI89 wild-type (WT) biofilms, AP193 induced a dose-dependent reduction in ThT fluorescence, indicating significant suppression of EM amyloid content (FIG. 12A, gray bars). At its highest dose, AP193 reduced the ThT fluorescence of WT biofilms to levels near those of the ΔcsgA strain, suggesting complete abrogation of curli formation. Residual fluorescence signals were therefore attributed to nonspecific ThT binding with components of the cell membrane. Additionally, synthetic α-sheet peptides did not suppress biofilm growth or demonstrate appreciable toxicity; rather, the reduction in EM amyloid content shifted a substantial proportion of bacteria from the biofilm state to the planktonic state (FIG. 12B). Peptide-treated biofilms displayed a more dispersed and soluble phenotype, with far less biomass adhered to glass slides after a gentle washing step (FIG. 12C). These effects were verified by RT-qPCR, which did not reveal any significant changes in csgA expression for biofilms grown in the presence of AP193 compared to peptide-free controls. UTI89 biofilms were also cultivated in the presence of an unstructured peptide, P1, which retains a mixture of L- and D-amino acids but lacks the α-sheet secondary structure of AP193. Biofilm amyloid content remained unaffected regardless of the concentration of P1 applied (FIG. 12D), establishing the importance of α-sheet structure in the mechanism of inhibition.

To extend the applicability of synthetic α-sheet peptides beyond the well-characterized UTI89 system, we obtained several *E. coli* isolates from pediatric patients who presented with urinary tract infections. As in the UTI89 WT system, AP193 caused a significant decrease in ThT fluorescence of the antibiotic resistant strains GERB 319 and GERB 337 (FIG. 12E), demonstrating the broad antimicrobial utility of synthetic α-sheet peptides irrespective of bacterial resistance profile.

Antibiotic Susceptibility Tests

The results above show that synthetic α-sheet peptides inhibit biofilm formation without inhibiting bacterial growth. As a result, bacteria within the peptide-treated biofilms are less tightly associated and a greater proportion of them reside in the planktonic state. An abundance of research has demonstrated that biofilm-associated bacteria are far less susceptible to antibiotic treatment than their planktonic counterparts, so we hypothesized that the "matrix loosening" effect of synthetic α-sheet peptides would render *E. coli* more vulnerable to antibiotic clearance.

Figure 13:
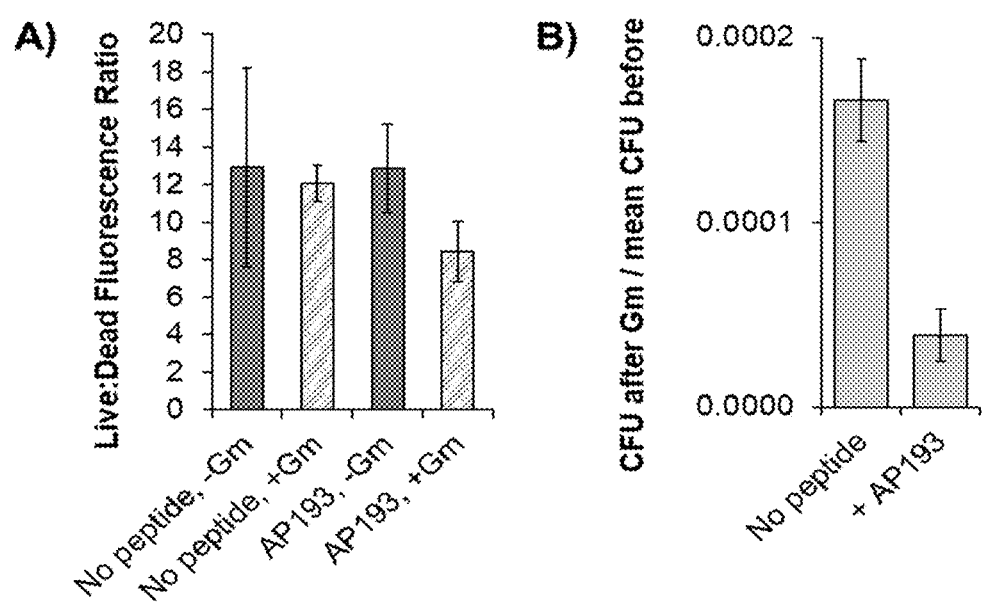
FIG. 13. Synthetic α-sheet peptides increase antibiotic susceptibility of uropathogenic *E. coli* biofilms, as measured by A) live/dead fluorescence ratio and (B) CFU counts. Error bars indicate standard deviation of the mean of at least three replicates.

To test this hypothesis, biofilms of *E. coli* UTI89 WT were grown in YESCA broth+4% DMSO in 48 well plates at 26° C. Media was removed 6 h prior to the end of the 48 h incubation period and replaced either with fresh media alone or fresh media containing 150 μg/mL gentamicin (Gm), an aminoglycoside antibiotic. After the 6 h incubation, biofilms were harvested by aspirating the planktonic cells, rinsing the biofilm once with PBS, and then resuspending the biofilm in PBS. Biofilm suspensions were homogenized with a probe sonicator and subjected to one of two processing protocols. In the first assay, the bacterial density of each biofilm suspension was normalized by absorbance at 670 nm and then bacteria were stained with Live/Dead (Syto9/propidium iodide) to obtain a fluorescent readout of viability. In the second assay, biofilm suspensions were serially diluted in sterile PBS and then plated on agar plates to obtain colony-forming unit (CFU) counts. Both approaches demonstrated that the synthetic α-sheet peptide AP193 improved the efficacy of Gm against *E. coli* UTI89 WT biofilms, as compared with peptide-free controls (FIG. 13A,B).

Immune Clearance Tests

Macrophages and other immune cells engulf invading microbes and digest them in the lysosome through a process known as phagocytosis. Previous work has demonstrated that bacteria in biofilms are less susceptible to phagocytosis than their free-swimming counterparts, likely due to the large size of the biofilm and the presence of structurally protective macromolecules in the EM. Synthetic α-sheet peptides compromise the strength of the EM by inhibiting curli formation, so this dispersion effect should increase the susceptibility of bacteria to phagocytosis by host immune cells.

Figure 14:
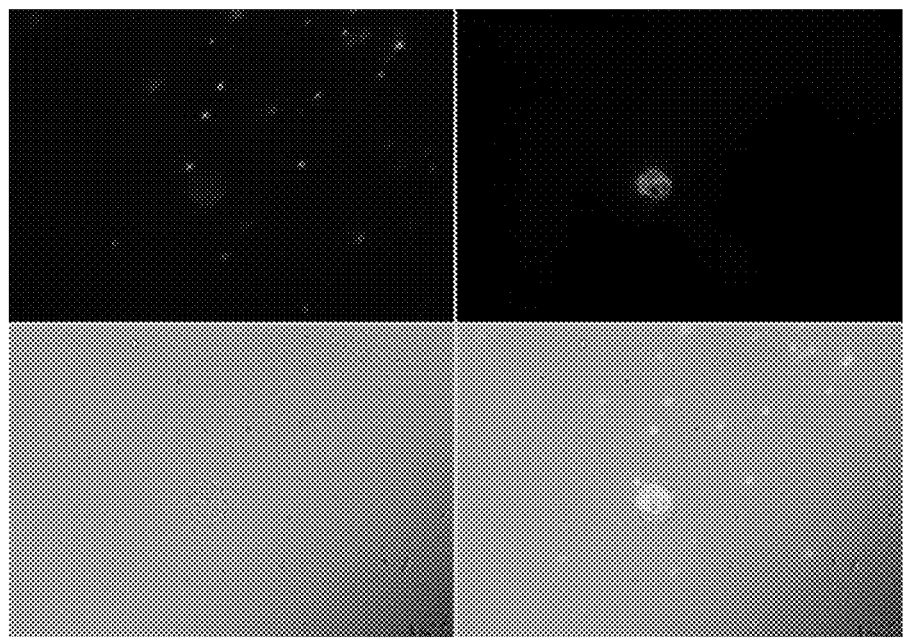
FIG. 14. The macrophages are not able to phagocytose biofilm-associated bacteria (A). Administration of AP193 breaks up the biofilms and yields a greater fraction of free-swimming bacteria that are susceptible to phagocytosis (B).
Figure 14:
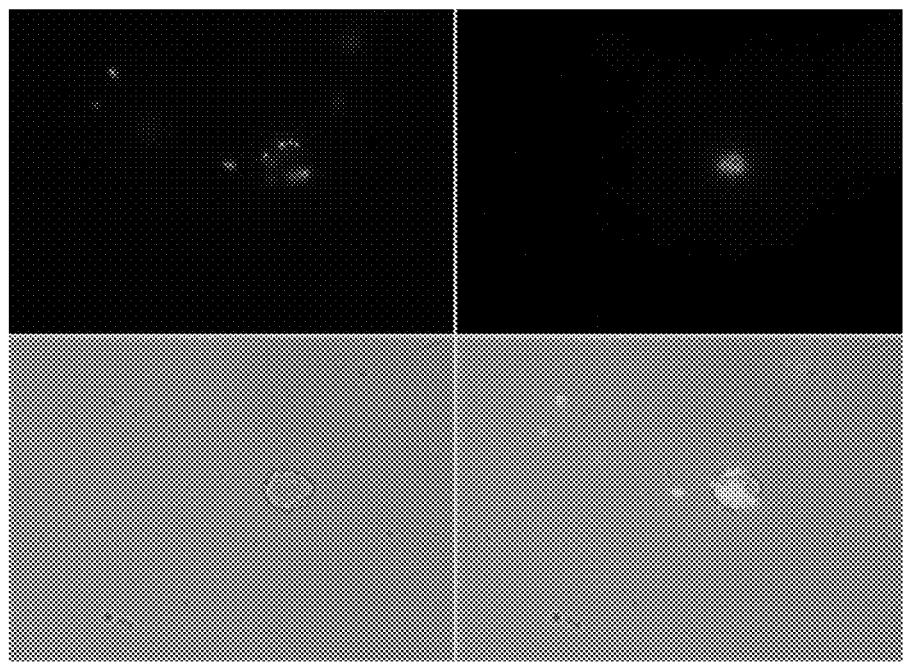

To investigate this proposition, biofilms were cultivated in the presence or absence of synthetic α-sheet peptides (shown for AP193 in FIG. 14) and then co-incubated with murine macrophages. A chromosome-based GFP derivative of *E. coli* UTI89, vsfGFP-9, was used to visualize the extent of phagocytosis in each case with flow cytometry. Murine monocyte/macrophage-like cells, RAW 264.7, were cultured in DMED+10% FBS at 37° C. in 75 cm² flasks. Biofilms were grown in 48 well plates for 48 h in YESCA broth+4% DMSO at 26° C. Planktonic cells were aspirated and biofilms rinsed and gently detached from plates using sterile PBS. The suspensions were combined in a 10:1 (bacteria: cell) ratio with RAW 264.7 cells and incubated for 30 min at 37° C. in PBS to allow uptake of bacteria by macrophages. Trypsin was added at a concentration of 0.25% and incubated for 10 min to remove any bacteria bound to the external surfaces of the RAW 264.7 cells. Free bacteria were removed by three PBS washes with low-speed centrifugation prior to resuspension in PBS+2% heat-inactivated PBS. Cells were then gated according to positive GFP (phagocytosed bacteria) using bacteria-free controls on a FACS Cantoll flow cytometer, and the percentage of cells positive for GFP was recorded and analyzed. Biofilms treated with synthetic α-sheet peptides were more susceptible to phagocytosis (FIG. 14).

*Pseudomonas aeruginosa* (Fap)

In *P. aeruginosa*, functional amyloids are comprised primarily of a protein known as FapC. As in *E. coli*, these fibers are assembled on the outside of cells with the assistance of several co-expressed chaperones and transporters, encoded in a single operon called fap, and they contribute to the recalcitrance of the biofilm matrix.

In Vitro Inhibition Assays

Figure 15:
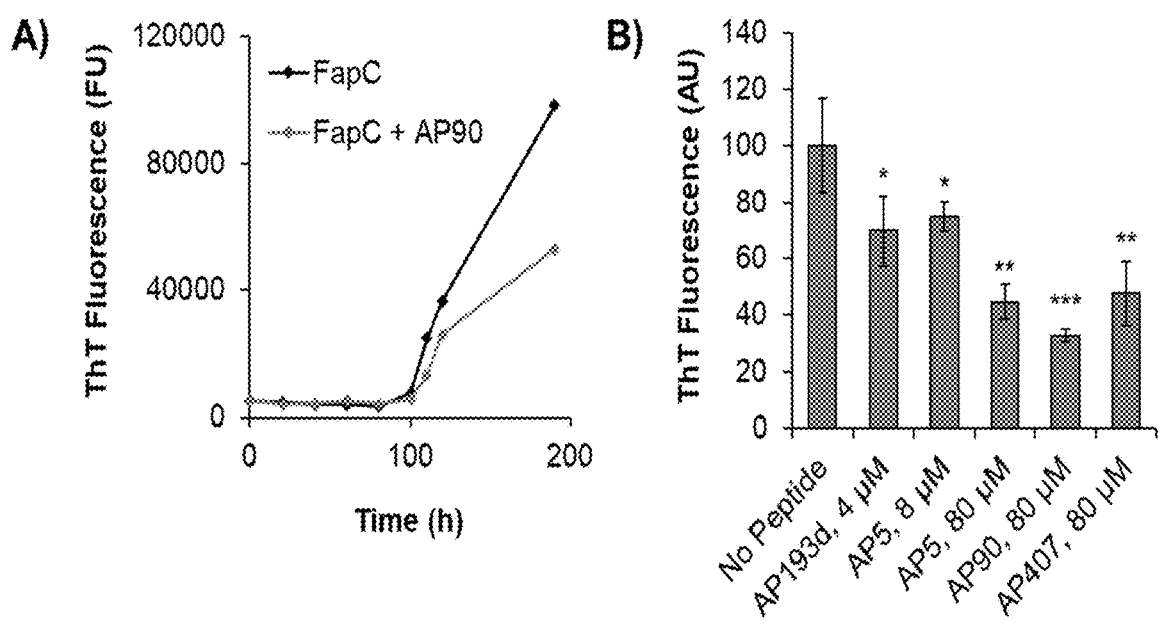
FIG. 15. Action of synthetic α-sheet peptides in the *P. aeruginosa* system. A) AP90 inhibits fibril formation of FapC in an in vitro ThT aggregation assay. (B) AP193, AP5, AP90, and AP407 significantly inhibit amyloid formation in *P. aeruginosa* PAO1 pFap biofilms. Error bars indicate standard deviation of the mean of at least three replicates. Significance values are $p<0.05$: *, $p<0.01$: , $p<0.001$: *.

To monitor aggregation of FapC, purified, recombinant FapC is desalted from a stock solution containing 6 M urea into 10 mM Tris buffer (pH 7.5) and diluted to a final concentration of 0.2 mg/mL. Samples are aliquoted into 96 well plates and incubated in a plate reader at 37° C. with shaking every 5 min. As previously, the fluorescence of ThT monitors protein fibril formation in real time. Synthetic α-sheet peptides may also be added to the reaction to determine whether they inhibit FapC fibril formation, as in the case of AP90 (FIG. 15A).

In Situ Inhibition Assays

The strain used in these experiments is a fap-overexpressing mutant of *P. aeruginosa* PAO1 WT called PAO1 pFap. The overexpression is generated by cloning the entire fap operon into a host expression vector, which is then transformed into PAO1 WT. In terms of phenotype and proteome, this strain is more representative of biofilms found in the lungs of cystic fibrosis patients than the wild-type strain. For in situ assays, overnight cultures from a single colony of freshly transformed PAO1 pFap were used to inoculate 96 well plates in the presence of synthetic α-sheet peptides in LB medium. As a control, biofilms of the deletion strain PAO1 Δfap were grown under the same conditions. Plates were covered and incubated at 37° C. for 48 h. After incubation, planktonic cells and media were gently removed from the biofilms by pipetting. The biofilms were rinsed once with PBS prior to staining with 20 μM ThT. Stained biofilms were resuspended by pipetting and sonication, and the fluorescence of ThT was measured at 448/485 nm in a plate reader. As shown in FIG. 15B, multiple synthetic α-sheet peptides substantially suppress the formation of Fap amyloid in these *P. aeruginosa* biofilms.

*Streptococcus mutans*

*Streptococcus mutans* is a bacterial species that predominates in the oral microbiome. *S. mutans* binds to the tooth surface, metabolizes sugars and produces acid, leading to cavity formation. *S. mutans* can also cause infectious endocarditis. Recent evidence suggests that *S. mutans* biofilms contain amyloid fibrils. To investigate the mechanism of functional amyloid formation in *S. mutans*, α-sheet peptides were compared to epigallocatechin gallate for their ability to inhibit fibril formation in *S. mutans*. Inhibition was demonstrated in a biofilm plate assay and on hydroxyapatite surfaces both in *S. mutans* alone and in bacteria from human saliva (data not shown). The observed inhibition suggests that an α-sheet mediated mechanism may be operative during functional amyloid formation.

In Situ Inhibition Assays

The peptides AP90, AP407, AP193, P411, and P1 were screened for their ability to inhibit amyloid fibril formation using an optimized ThT assay for *S. mutans* biofilms. Briefly, *S. mutans* UA159 overnight cultures were diluted in BHI medium with 30 mM sucrose and 1% (v/v) EC Oxyrase® to ensure an oxygen-limited environment. Inocula were then mixed with inhibitors in water, or only water for blank conditions. Biofilms were cultivated at 37° C. in 96 well plates. After 28 h, planktonic cells and media were aspirated. Biofilms were rinsed once with PBS and then resuspended in a solution of 22 μM ThT in PBS. Stained biofilm suspensions were transferred to a new microtiter plate and their fluorescence was measured in a plate reader.

Figure 16:
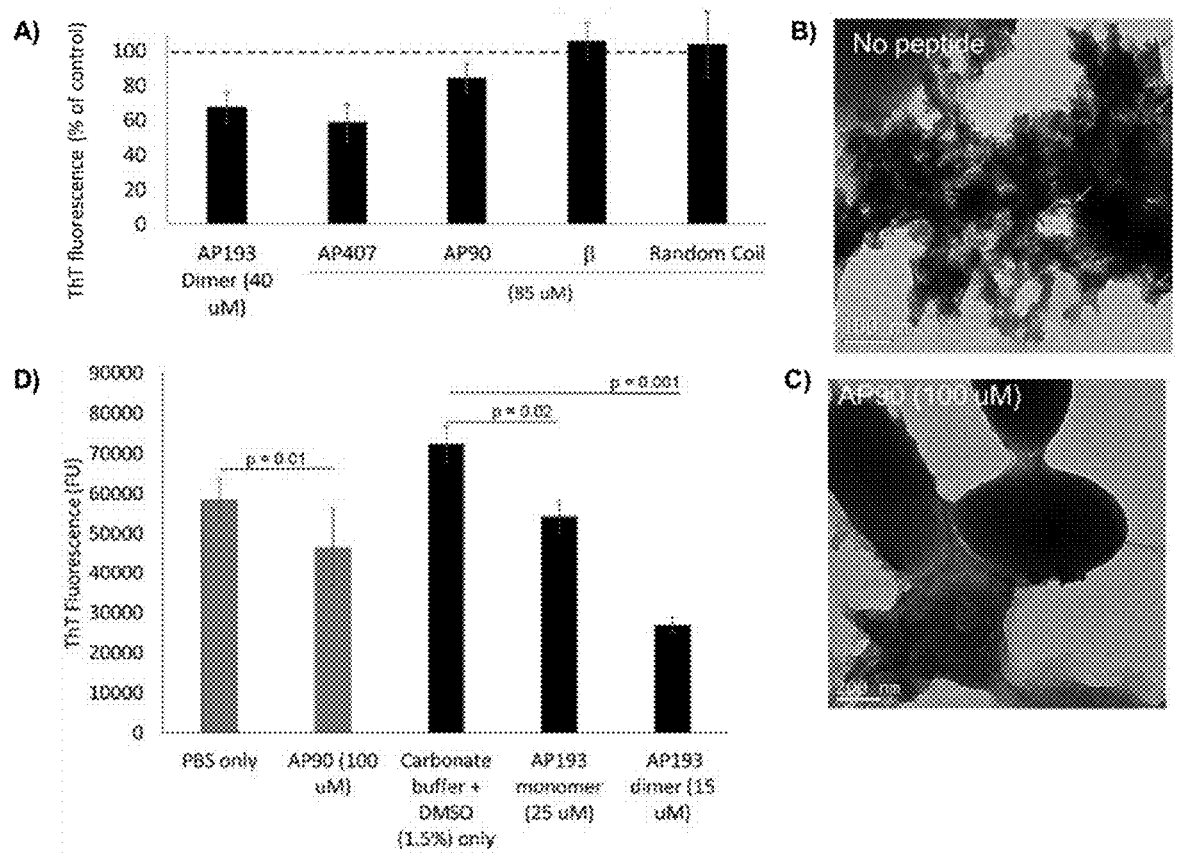
FIG. 16. Synthetic α-sheet peptides as a novel anti-biofilm agent for the dental pathogen, *S. mutans*. A) ThT fluorescence of *S. mutans* biofilms decreases upon addition of synthetic α-sheet peptides AP193, AP407, and AP90. However, the β-sheet and random coil control peptides showed no significant decrease in ThT fluorescence. TEM imaging of biofilm with B) no peptide and C) AP90 (100 μM) revealed a loss of fibrillar material (arrows) upon addition of AP90. D) synthetic α-sheet peptides added to *S. mutans* grown on hydroxyapatite ceramic particles led to significant decreases in ThT fluorescence.

Several synthetic peptides caused significant suppression in the amyloid content of *S. mutans* biofilms, and the effect was specific to those with α-sheet structure. AP193 at 40 μM decreased ThT fluorescence by 33% (p=0.007). A 42% decrease in ThT fluorescence compared to the control was seen with 85 μM AP407 (p<0.0001). AP90 caused a 16% decrease in ThT fluorescence at 85 μM (p=0.017). However, the β-sheet hairpin control P411 and the random coil control P1 had no significant effect (FIG. 16A).

The phenotypic effects of synthetic α-sheet peptides were determined using TEM. Distinct fibrillar structures were found in the extracellular material surrounding cells with no peptide present, but such structures were not observed around cells when α-sheet peptide AP90 was present (FIG. 16B,C).

To assess peptide inhibition of amyloid fibrils in *S. mutans* adhered to tooth-like surfaces, biofilms were grown on ceramic-hydroxyapatite particles. Hydroxyapatite is the primary mineral present in the structure of a tooth, so this assay is a more physiologically relevant model of *S. mutans* accumulation. ThT fluorescence of adhered biofilms was determined after 24 h of growth. Synthetic α-sheet peptides were added to medium and hydroxyapatite ceramic particles prior to cell growth. Addition of AP90 (100 μM) led to a 20% decrease in ThT fluorescence, comparable to decreases seen in the plate assay. Both AP193 monomer and dimer caused significant decreases in ThT fluorescence (23% and 63%, respectively; FIG. 16D).

Polydopamine Coating for Conjugation of α-Sheet Peptides to Biomaterials

We have conjugated α-sheet peptides to other functional molecules to enhance their efficacy at the site of biofilm infection, i.e., the surface of biomedical implants. To this end, we used a polydopamine (PDA) coating approach to facilitate attachment of α-sheet peptides to biomedical implant materials. The resulting polydopamine-grafted peptide materials (PGPMs) were then tested for their ability to suppress amyloid formation and increase antibiotic susceptibility. Biofilms form on a wide array of medical device implants including titanium (TiO2), an inorganic material often used for orthopedic implants, and polystyrene (PS), an organic material often used in catheters. Titanium plates (grade 4, 10 mm×10 mm) were cleaned using successive rounds of polishing followed by ultrasonic cleaning in acetone, ethanol, and water. Both TiO2 and PS were rinsed thoroughly with distilled water prior to use. Dopamine (2 mg/mL) was dissolved in 10 mM Tris-HCl (pH 8.5) and substrates were dipped into the solution for 24 hours with stirring. Substrates were rinsed again with water, dried by $N_2$ gas, and stabilized at 40° C. for 2 hours. Control substrates were also generated, using incubation in Tris buffer without dopamine.

For α-sheet peptide grafting, 0.5 mg/mL peptide (e.g. AP90, AP193, or P1 as a control) was dissolved in 10 mM Tris pH 8.0 and then applied to PDA-coated substrates for overnight reaction (18 hours). After conjugation, PGPMs were rinsed with water and dried by $N_2$ gas. Peptide functionalization was verified by two methods. First, the concentration of peptide remaining in solution after conjugation was measured by NanoOrange™ assay to determine coupling efficiency and surface density. Second, accessibility of α-sheet peptides on the surface was determined by immunofluorescence; PGPMs were blocked with 5% BSA solution for 12 h, incubated with AlexaFluor®568-conjugated Pac53 antibody (which recognizes α-sheet peptides), and then washed and imaged on a fluorescent microscope to ensure attachment to the disks.

Figure 17:
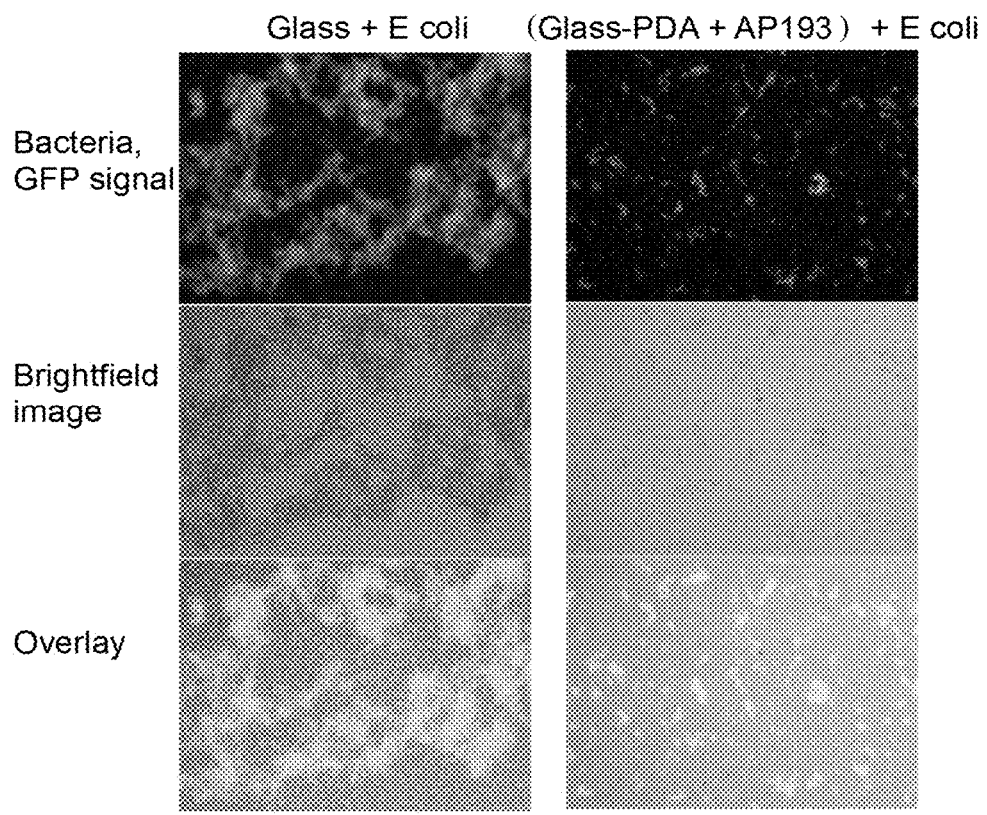
FIG. 17. Bacterial adherence and growth of biofilm on glass disks and decreased adhesion of bacteria (GFP signal) and biofilm and amyloid formation (Brightfield image) when glass is coated with α-sheet peptides, shown for dimeric AP193. This is a model for biofilm formation on implanted devices such as prosthetic joints.

PGPMs were tested against amyloid-forming bacterial strains for their ability to inhibit amyloid formation in the biofilm EM. Both TiO2- and PS-based materials 10 mm×10 mm coupons, were placed upright in 200 μL bacterial cultures in a 48 well plate. Plates were incubated at the same temperature and for the same length of time as in previous biofilm assays. After incubation, loosely adhered cells and media were rinsed from the biofilm surface by dipping in PBS, and PGPMs were transferred to new wells containing 400 μL PBS. The plates were sonicated for 10 minutes in a water bath to detach biofilms from the surface of the PGPMs, and then the resulting suspensions were supplemented with 20 μM ThT and incubated in the dark for 20 minutes. Complete detachment of biofilms were confirmed by crystal violet (CV) staining of the removed PGPM coupons. After incubation with ThT, 100 μL of each stained biofilm suspension was transferred in triplicate to wells of a black-walled 96 well plate. In addition to PGPMs functionalized with α-sheet peptides, several other controls were tested in this procedure: (1) non-functionalized materials (plain TiO2 and PS); (2) PDA-only materials that lack α-sheet peptides; and (3) PGPMs functionalized with the random coil control peptide, P1, instead of α-sheet peptides. A dramatic drop in the amount of bacterial biofilm on an α-sheet coated glass disk, was seen using AP193 as an exemplary embodiment (FIG. 17). This is a model for biofilm formation on implanted devices such as prosthetic joints.

MATERIALS AND METHODS

Computational Peptide Design and Synthesis

The goal of our computational design process is stable, soluble α-sheet hairpin peptide designs (α-strand—turn—α-strand to form a small α-sheet hairpin). To do this we designed a turn to support the necessary geometrical requirements of α-sheet and strands comprised of alternating L/D amino acid sequences, as L-amino acids favor $α_R$ conformations and the corresponding D-amino acids favor $α_L$ conformations. In addition, amino acids were chosen to favor particular packing across the strands as well as for solubility. For this study we focused on variants to our the AP90 design: AP401, reversed chirality with respect to AP90; AP407, contains a disulfide bond near the turn; AP5, a scrambled sequence maintaining the L/D α-sheet templating; and AP193, a variant to support different chemical coupling reactions (Table 2). To confirm stability of the α-sheet structure, multiple short MD simulations were performed.[25] The peptides were then produced using solid phase peptide synthesis on Rink amide resin with Fmoc chemistry and HBTU activation.[39] The resulting resin-bound peptides were cleaved and side chains deprotected with TFA/TIPS/H$_2$O (95:2.5:2.5) and precipitated with cold ether. Crude peptides were purified by RP-HPLC to ~98% purity (Phenomenex™ 5 µm C12 100 Å semiprep column). Purified peptides were confirmed by mass spectrometry (MS) on a Bruker Esquire Ion Trap electrospray mass spectrometer, and peptide stocks were lyophilized for storage at −20° C. For assays, peptide stocks were thawed and reconstituted in filtered ddH$_2$O to a concentration of 2 mg/mL.

Biofilm Screening Assays

Overnight cultures of *S. aureus* (see Table 1 for a list of strains used in this study) were spun down and re-suspended in fresh Luria-Bertani (LB) media to an optical density of 0.1 (600 nm). These cultures were then mixed with reconstituted peptide (or water, in the case of controls) and aliquoted in quadruplicate into wells of a clear 48-well plate (Corning, TC-treated polystyrene). The final concentration of peptide in each well was 80 µM, unless otherwise noted. Plates were covered and biofilms were grown at 37° C. for 24 hours with gentle rocking. At this time, medium and planktonic cells were removed from wells using a vacuum and the remaining adherent biofilms were rinsed once with PBS (BupH™, Thermo Scientific). Thioflavin T (ThT), an established fluorescent label for amyloid fibrils[40], was then added to each well at a concentration of 22 µM and biofilms were incubated statically for 4 hours at room temperature. The solution was then removed from the wells and PBS was added with vigorous pipetting to detach biofilms from the plate surface. Plates were shaken at high speed for 1 minute on a plate shaker to detach any remaining biofilm material and homogenize the samples. The detached biofilm suspensions were transferred to a 96-well black-walled plate (Corning, TC-treated polystyrene) and ThT fluorescence was read at 438/495 nm on a Perkin-Elmer Enspire™ plate reader. Fluorescence measurements were corrected by subtracting the background intensity of identical samples without ThT. For calculation of live:dead cell ratios, biofilm suspensions were prepared as described above and cells were stained with a 1:1 mixture of Syto9 and propidium iodide (LIVE/DEAD BacLight™ Bacterial Viability Kit, Thermo Scientific). After 15 minutes of incubation at room temperature, fluorescence ratios of the two dyes were determined using a Perkin-Elmer Enspire™ plate reader.

Microscopy

For fluorescence microscopy studies, *S. aureus* MN8+ mCherry™ overnight cultures were diluted to an optical density of 0.1 (600 nm) and combined with α-sheet peptide inhibitors as described above; the final concentration of peptide was 80 µM. Biofilms were grown in sixteen-well chambered coverglass plates (Lab-Tek® Chamber Slides) and analyzed on a Zeiss Axio™ Observer inverted microscope after gentle washing and fixing with 4% paraformaldehyde. For atomic force microscopy (AFM) studies, the synthetic PSMα1 peptide was prepared to a concentration of 440 µM (as described below) and incubated at 37° C. for 24 h. The resulting amyloid fibrils were applied directly to freshly cleaved mica and incubated for 2 h. Samples were rinsed five times with ddH$_2$O and allowed to dry prior to imaging on a Bruker ICON™ atomic force microscope using tapping mode and a ScanAsyst™ silicon tip. Images were analyzed using Gwyddion™ software (Czech Metrology Institute). For transmission electron microscopy (TEM) studies, biofilms were grown in 48-well plates as described above. After 24 h of growth, biofilms were rinsed with PBS, scraped from the sides of the plate, spotted onto formvar-coated copper grids, stained with 2% uranyl acetate for 2 min, and imaged on a JEOL™-1230 microscope with an AMT XR80 camera.

Preparation of PSMα1 Peptide

Lyophilized peptide stocks of synthetic PSMα1 (fMGI-IAGIIKVIKSLIEQFTGK (SEQ ID NO:7), where f denotes formylation, Ontores Biotechnologies) were prepared as previously described[15] to eliminate aggregates from lyophilization prior to assay. Briefly, dry PSMα1 peptide was dissolved to a concentration of 10 mg/mL in a 1:1 mixture of trifluoroacetic acid (TFA) and hexafluoroisopropanol (HFIP). Ice-cold HFIP was then added to dilute PSMs to 1 mg/mL and the sample was sonicated for 10 minutes. Solvent TFA/HFIP was removed by air stream and then speedvac at room temperature before storage at −20° C. Prior to assay, PSMα1 aliquots were prepared by dissolving the peptide in ice cold HFIP to a concentration of 10 mg/mL, vortexing, sonicating for 5 minutes, and incubating for 25 minutes on ice. The peptide was then dried using a stream of air and a speedvac at room temperature to make dry stocks of PSMα1. At this point the stock peptide was prepared differently depending on the experiment to be performed. The peptide is very hydrophobic and requires organic solvent for solubilization. The default preparation was to solubilize the peptide in DMSO; however, DMSO has strong UV absorption so HFIP was used for the CD experiments and corresponding ThT aggregation assay.

Circular Dichroism Spectroscopy

Stock PSMα1 in HFIP was diluted to a concentration of 30 µM in potassium phosphate buffer (KH$_2$PO$_4$, pH 5) with and without 20 µM ThT, resulting in 0.13% v/v HFIP in the diluted samples. To determine the timing of CD measurements, PSMα1 polymerization was monitored over time. 150 µL samples with and without ThT were aliquoted into individual wells of a black-walled 96 well plate (Corning) and the plate was incubated at 37° C. inside a Perkin-Elmer Enspire™ plate reader. ThT fluorescence was measured every hour after shaking. ThT-free samples were periodically withdrawn from the plate for CD measurements at 37° C. on a Jasco J-715 spectrophotometer with 1 mm cuvettes. The resulting spectra were smoothed and deconvoluted (Savitsky-Golay method, convolution width 25) using Jasco Spectra Analysis software.

PSMα1 Fibrillization Assay with Added Inhibitors

To solubilize the PSMs for the aggregation assay, filtered DMSO was added to the dry PSMα1 stock to achieve a 20 mg/mL solution. Samples were then further diluted by addition of ddH$_2$O+22 µM ThT with and without added α-sheet peptide designs (at 1:3 or 1:4 molar ratio of PSM: inhibitor) to a final concentration of 30 µM PSMα1 in all cases. 50 µL samples (pH 5.5) were aliquoted into individual wells of a 384-well black-walled plate (BrandTech, non-treated polystyrene). The plate was incubated in a 37° C. Perkin-Elmer Enspire™ plate reader and ThT fluorescence was measured every 30-60 minutes after shaking.

Immobilization and Solution Binding

Figure 9:
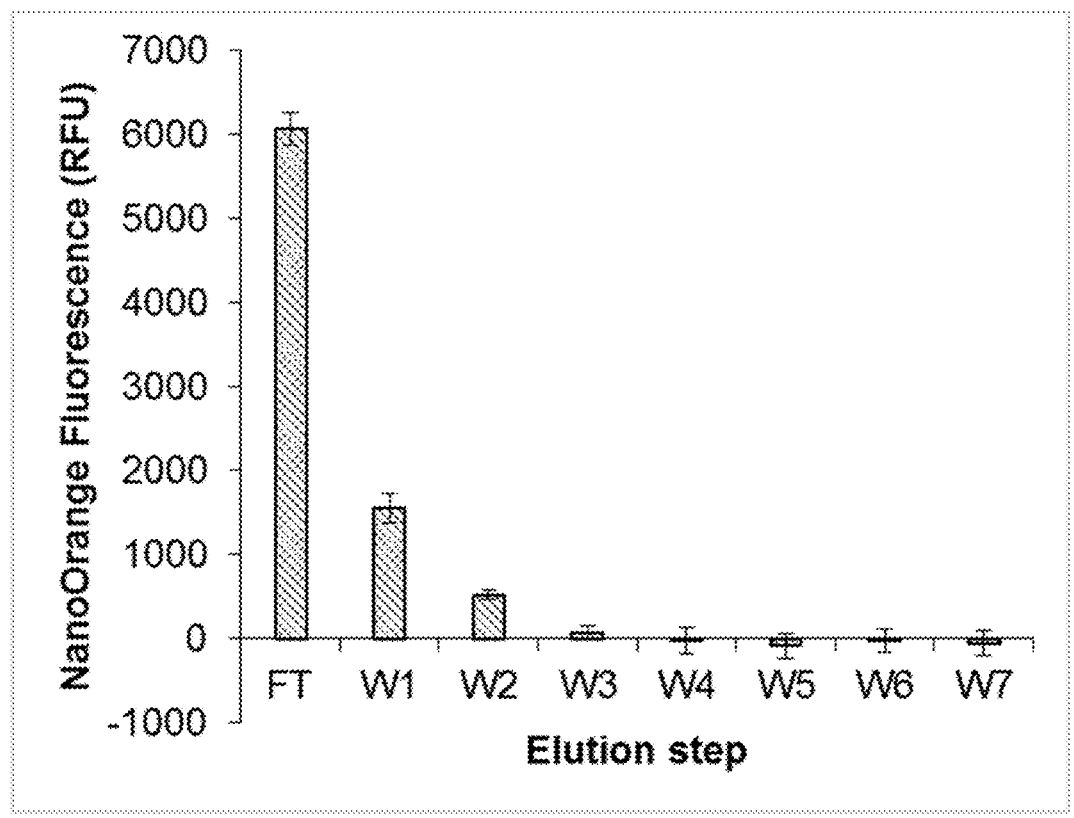
FIG. 9. Graph showing representative removal of detectable protein in column binding assays. Wash steps in the column-binding assay are sufficient to remove all detectable protein in the eluent. By the seventh wash, protein concentrations fall below the fluorescent-detectable level of 10 ng/mL. The data are for fresh PSMα1 (0 h) samples applied to the column, but are representative of all column binding assays.

Peptide designs were immobilized on Pierce Amino Link agarose beads in a Pierce spin column (Thermo Fisher Scientific) according to a previously established protocol.[25] Briefly, the designed peptide AP193 (FIG. 9) was dissolved to a concentration of 250 µM in PBS+25% v/v DMSO+50 mM NaCNBH$_3$ and allowed to couple to the aldehyde-functionalized resin overnight at 4° C. Residual active sites were blocked with 1 M Tris HCl+50 mM Na CNBH$_3$ for 4 h at 25° C. Meanwhile, PSMα1 peptide samples were prepared as above (see "PSM fibrillization assay") and incubated at 37° C. After 0, 24, and 48 h, a sample of 200 µL PSMα1 was removed from the microtiter plate and added to a prepared spin column; these PSMα1 samples were allowed to bind to the peptide-functionalized resin beads for 2 h at 25° C. The solution was then collected by centrifugation (flow-through, FT). The beads were re-suspended in 300 µL PBS, vortexed to obtain a uniform slurry, and then the solution was collected by centrifugation (wash 1, W1). This wash step was performed a total of 7 times, until no remaining protein was detected in the eluent (FIG. 9). Each of the wash (W1-W7) and flow-through (FT) solutions was retained for analysis with the NanoOrange® Protein Quantitation Kit (Thermo Fisher Scientific), a fluorescent detection method that enabled quantitation of the total protein concentration in each sample. The mass of PSMα1 in each eluent was calculated and summed, and then these values were subtracted from the mass of PSMα1 applied to the column in order to obtain a mass balance.

Biolayer Interferometry

All biolayer interferometry (BLI) experiments were performed on a BLItz™ biosensor system (ForteBio) using aminopropylsilane (APS) sensors. Sensors were hydrated in ddH$_2$O+22 µM ThT for 10 minutes prior to use. Designed peptides (dissolved in ddH$_2$O+22 µM ThT) were loaded onto the APS tip, a baseline was established in ddH$_2$O+22 µM ThT, and then the association of PSMα1 (prepped with DMSO+ddH$_2$O+22 µM ThT, as in the fibrillization assay at various pre-incubation times) was monitored over a period of three minutes. Dissociation was subsequently measured in ddH$_2$O+22 µM ThT, and the equilibrium dissociation constant ($K_D$) was calculated using the BLItz™ analysis software (ForteBio).

REFERENCES

1. Allegranzi, B. et al. Burden of endemic health-care-associated infection in developing countries: systematic review and meta-analysis. *The Lancet* 377, 228-241 (2011).
2. Centers for Disease Control and Prevention. *National and state healthcare associated infections progress report*. (Centers for Disease Control and Prevention, 2016).
3. Klevens, R. M. et al. Estimating health care-associated infections and deaths in U.S. hospitals, 2002. *Public Health Rep.* Wash. DC 1974 122, 160-166 (2007).
4. Bryers, J. D. *Medical Biofilms. Biotechnol. Bioeng.* 100, 1-18 (2008).
5. Bagge, N. et al. *Pseudomonas aeruginosa* biofilms exposed to imipenem exhibit changes in global gene expression and beta-lactamase and alginate production. *Antimicrob. Agents Chemother.* 48, 1175-1187 (2004).
6. Ma, H. & Bryers, J. D. Non-invasive determination of conjugative transfer of plasmids bearing antibiotic-resistance genes in biofilm-bound bacteria: effects of substrate loading and antibiotic selection. *Appl. Microbiol. Biotechnol.* 97, 317-328 (2013).
7. Mah, T. F. & O'Toole, G. A. Mechanisms of biofilm resistance to antimicrobial agents. *Trends Microbiol.* 9, 34-39 (2001).
8. Stewart, P. S. & Costerton, W. J. Antibiotic resistance of bacteria in biofilms. *The Lancet* 358, 135-138 (2001).
9. Lewis, K. Platforms for antibiotic discovery. *Nat. Rev. Drug Discov.* 12, 371-387 (2013).
10. Klevens, R. M. et al. Changes in the Epidemiology of Methicillin-Resistant *Staphylococcus aureus* in Intensive Care Units in US Hospitals, 1992-2003. *Clin. Infect. Dis.* 42, 389-391 (2006).
11. Klevens, R. M. et al. Invasive methicillin-resistant *Staphylococcus aureus* infections in the United States. *JAMA* 298, 1763-1771 (2007).
12. Wang, R. et al. Identification of novel cytolytic peptides as key virulence determinants for community-associated MRSA. *Nat. Med.* 13, 1510-1514 (2007).
13. Joo, H.-S., Cheung, G. Y. C. & Otto, M. Antimicrobial activity of community-associated methicillin-resistant *Staphylococcus aureus* is caused by phenol-soluble modulin derivatives. *J. Biol. Chem.* 286, 8933-8940 (2011).
14. Periasamy, S. et al. How *Staphylococcus aureus* biofilms develop their characteristic structure. *Proc. Natl. Acad. Sci.* 109, 1281-1286 (2012).
15. Schwartz, K., Syed, A. K., Stephenson, R. E., Rickard, A. H. & Boles, B. R. Functional amyloids composed of phenol soluble modulins stabilize *Staphylococcus aureus* biofilms. *PLoS Pathog.* 8, e1002744 (2012).
16. DePas, W. H. & Chapman, M. R. Microbial manipulation of the amyloid fold. *Res. Microbiol.* 163, 592-606 (2012).
17. Syed, A. K. & Boles, B. R. Fold modulating function: bacterial toxins to functional amyloids. *Front. Microbiol.* 5, 401 (2014).
18. Taglialegna, A., Lasa, I. & Valle, J. Amyloid Structures as Biofilm Matrix Scaffolds. *J. Bacteriol.* 198, 2579-2588 (2016).
19. Knowles, T. P. J., Vendruscolo, M. & Dobson, C. M. The amyloid state and its association with protein misfolding diseases. *Nat. Rev. Mol. Cell Biol.* 15, 384-396 (2014).
20. Bemporad, F. & Chiti, F. Protein Misfolded Oligomers: Experimental Approaches, Mechanism of Formation, and Structure-Toxicity Relationships. *Chem. Biol.* 19, 315-327 (2012).
21. Kayed, R. et al. Common Structure of Soluble Amyloid Oligomers Implies Common Mechanism of Pathogenesis. *Science* 300, 486-489 (2003).
22. Armen, R. S., DeMarco, M. L., Alonso, D. O. V. & Daggett, V. Pauling and Corey's α-pleated sheet structure may define the prefibrillar amyloidogenic intermediate in amyloid disease. *Proc. Natl. Acad. Sci. U.S.A.* 101, 11622-11627 (2004).
23. Armen, R. S., Alonso, D. O. V. & Daggett, V. Anatomy of an Amyloidogenic Intermediate: Conversion of β-Sheet to α-Sheet Structure in Transthyretin at Acidic pH. *Structure* 12, 1847-1863 (2004).
24. Daggett, V. Alpha-sheet: The toxic conformer in amyloid diseases? *Acc. Chem. Res.* 39, 594-602 (2006).
25. Hopping, G. et al. Designed α-sheet peptides inhibit amyloid formation by targeting toxic oligomers. *eLife* 3, e01681 (2014).
26. Kellock, J., Hopping, G., Caughey, B. & Daggett, V. Peptides Composed of Alternating L- and D-Amino Acids Inhibit Amyloidogenesis in Three Distinct Amyloid Systems Independent of Sequence. *J. Mol. Biol.* 428, 2317-2328 (2016).
27. Horsburgh, M. J. et al. σB modulates virulence determinant expression and stress resistance: characterization of a functional rsbU strain derived from *Staphylococcus aureus* 8325-4. *J. Bacteriol.* 184, 5457-5467 (2002).
28. Berlon, N. R. et al. Clinical MRSA isolates from skin and soft tissue infections show increased in vitro production of phenol soluble modulins. *J. Infect.* 71, 447-457 (2015).
29. Peschel, A. & Otto, M. Phenol-soluble modulins and staphylococcal infection. *Nat. Rev. Microbiol.* 11, 667-673 (2013).

30. Schleeger, M. et al. Amyloids: From molecular structure to mechanical properties. *Polymer* 54, 2473-2488 (2013).
31. Lee, C. C., Walters, R. I., & Murphy, R. M. Reconsidering the mechanism of polyglutamine peptide aggregation. *Biochemistry.* 46, 12810-12820 (2007).
32. Chen, S.; Ferrone, F. A.; Wetzel, R. Huntington's disease age-of onset linked to polyglutamine aggregation nucleation. *Proc. Natl. Acad. Sci. U.S.A.,* 99, 11884-11889 (2002).
33. Gorman, P. M.; Yip, C. M.; Fraser, P. E.; Chakrabartty, A. Alternate aggregation pathways of the Alzheimer beta-amyloid peptide: A beta association kinetics at endosomal pH. *J. Mol. Biol.,* 325, 743-757 (2003).
34. Marinelli, P., Pallares, I., Navarro, S. & Ventura, S. Dissecting the contribution of *Staphylococcus aureus* α-phenol-soluble modulins to biofilm amyloid structure. *Sci. Rep.* 6, 34552 (2016).
35. Schwartz, K., Ganesan, M., Payne, D. E., Solomon, M. J. & Boles, B. R. Extracellular DNA facilitates the formation of functional amyloids in *Staphylococcus aureus* biofilms. *Mol. Microbiol.* 99, 123-134 (2016).
36. Stewart, P. S. Mechanisms of antibiotic resistance in bacterial biofilms. *Int. J. Med. Microbiol.* 292, 107-113 (2002).
37. Towse, C.-L., Hopping, G., Vulovic, I., & Daggett, V. Nature versus design: The conformational propensities of D-amino acids and the importance of side chain chirality. *Prot. Eng. Des. Sel.* 27, 447-455 (2014).
38. Childers, M. C., Towse, C.-L., & Daggett, V. The effect of chirality and steric hindrance on intrinsic backbone conformational propensities: Tools for protein design. *Prot. Eng. Des. Sel.* 29, 271-280 (2016).
39. Stowikowski, M. & Fields, G. B. Introduction to Peptide Synthesis. *Curr. Protoc. Prot. Sci.* Unit-18.1 (2002).
40. LeVine, H. Thioflavine T interaction with synthetic Alzheimer's disease beta-amyloid peptides: detection of amyloid aggregation in solution. *Protein Sci.* 2, 404-410 (1993).

We claim:

1. A peptide consisting of the amino acid sequence selected from the group consisting of:
    Ac-rGeMnLsWmneysGwTmNlKmGr-NH2 (SEQ ID NO:2);and
    Ac-RGEmNlCwMNEYSGWcMnLkMGR-NH2 (SEQ ID NO:3);
        wherein residues in lower-case are D amino acids, residues in upper case are L amino acids, and G residues are achiral.

2. A medical device comprising the peptide of claim 1 coated on a surface of the medical device.

3. The medical device of claim 2, the medical device is selected from the group consisting of prosthetic heart valves, cardiac pacemakers, cerebrospinal fluid shunts, urinary catheters, intravascular catheters, ocular prostheses, and intrauterine contraceptive devices.

4. A method for treating a bacterial infection, comprising administering to a subject with a bacterial infection an amount of the peptide of claim 1 effective to treat the bacterial infection.

5. The method of claim 4, wherein the bacterial infection comprises a bacterial biofilm, and wherein the treating comprises disruption of the biofilm.

6. The method of claim 4, wherein the bacterial infection comprises an *Escherichia coli*, a *Pseudomonas aeruginosa*, or a *Staphylococcus aureus* bacterial infection.

7. The method of claim 4, wherein the bacterial infection comprises a drug or multi-drug resistant bacterial infection.

8. The method of claim 4, wherein the bacterial infection is contracted during hospitalization.

9. A method for limiting development of bacterial biofilm, comprising administering to a subject at risk of a bacterial infection comprising biofilm formation with an amount of the peptide of claim 1 effective to limit development of the bacterial biofilm, wherein the subject is undergoing a surgical procedure.

10. The method of claim 9, wherein the surgical procedure comprises placement of a medical device in the subject.

11. The method of claim 10, wherein the medical device is selected from the group consisting of prosthetic heart valves, cardiac pacemakers, cerebrospinal fluid shunts, urinary catheters, intravascular catheters, ocular prostheses, and intrauterine contraceptive devices.

12. The method of claim 11, wherein the peptide is placed on the medical device prior to placement of the medical device in the subject.

* * * * *